(12) United States Patent
Tachas

(10) Patent No.: US 9,885,048 B2
(45) Date of Patent: Feb. 6, 2018

(54) METHOD FOR REDUCING CIRCULATING LEUKOCYTES IN A HUMAN SUBJECT

(71) Applicant: Antisense Therapeutics Ltd, Toorak, Victoria (AU)

(72) Inventor: George Tachas, Kew (AU)

(73) Assignee: Antisense Therapeutic, Ltd, Toorak, Victoria (AU)

( * ) Notice: Subject to any disclaimer, the term of this patent is extended or adjusted under 35 U.S.C. 154(b) by 0 days.

(21) Appl. No.: 15/046,352

(22) Filed: Feb. 17, 2016

(65) Prior Publication Data

US 2016/0244768 A1 Aug. 25, 2016

Related U.S. Application Data

(63) Continuation of application No. 13/823,101, filed as application No. PCT/AU2011/001205 on Sep. 19, 2011, now abandoned.

(60) Provisional application No. 61/384,153, filed on Sep. 17, 2010.

(51) Int. Cl.
| | |
|---|---|
| *C12N 15/113* | (2010.01) |
| *A61K 31/7125* | (2006.01) |
| *A61K 31/7105* | (2006.01) |
| *A61K 35/28* | (2015.01) |
| *A61K 38/19* | (2006.01) |

(52) U.S. Cl.
CPC ...... *C12N 15/1138* (2013.01); *A61K 31/7105* (2013.01); *A61K 31/7125* (2013.01); *A61K 35/28* (2013.01); *A61K 38/193* (2013.01); *C12N 2310/11* (2013.01); *C12N 2310/315* (2013.01); *C12N 2310/321* (2013.01); *C12N 2310/322* (2013.01); *C12N 2310/3341* (2013.01); *C12N 2310/341* (2013.01); *C12N 2310/344* (2013.01); *C12N 2310/346* (2013.01)

(58) Field of Classification Search
CPC ............. C12N 15/111; C12N 15/1138; C12N 2310/11
See application file for complete search history.

(56) References Cited

U.S. PATENT DOCUMENTS

| | | |
|---|---|---|
| 6,258,790 B1 | 7/2001 | Bennett et al. |
| 2010/0119480 A1 | 5/2010 | Klinger et al. |

FOREIGN PATENT DOCUMENTS

| | | |
|---|---|---|
| WO | WO 2000/039292 A2 | 7/2000 |
| WO | WO 2008/017025 A2 | 2/2008 |

OTHER PUBLICATIONS

Kummer et al. (Biochem. Pharm. (2006) 72:1460-1468).*
International Search Report mailed Oct. 18, 2011 for International Patent Application No. PCT/AU2011/001205.
Written Opinion mailed Oct. 18, 2011 for International Patent Application No. PCT/AU2011/001205.
Engelhardt et al. (Journal of Clinical oncology, 1999; vol. 17(7): abstract, 2 pages).
Machine translation of Wo 2000039292, 7 pages. (WO 2000039292 was publically available in 2000).

* cited by examiner

*Primary Examiner* — J. E. Angell
(74) *Attorney, Agent, or Firm* — Knobbe, Martens, Olson & Bear, LLP

(57) ABSTRACT

The present disclosure relates to a method for treatment or prevention of diseases have an increased level of insulin-like growth factor I (IGF-I). The method comprises administration of a growth hormone (GH) variant having antagonistic activity in combination with an oligonucleotide targeted to growth hormone receptor (GHR) to a subject in need.

8 Claims, 1 Drawing Sheet

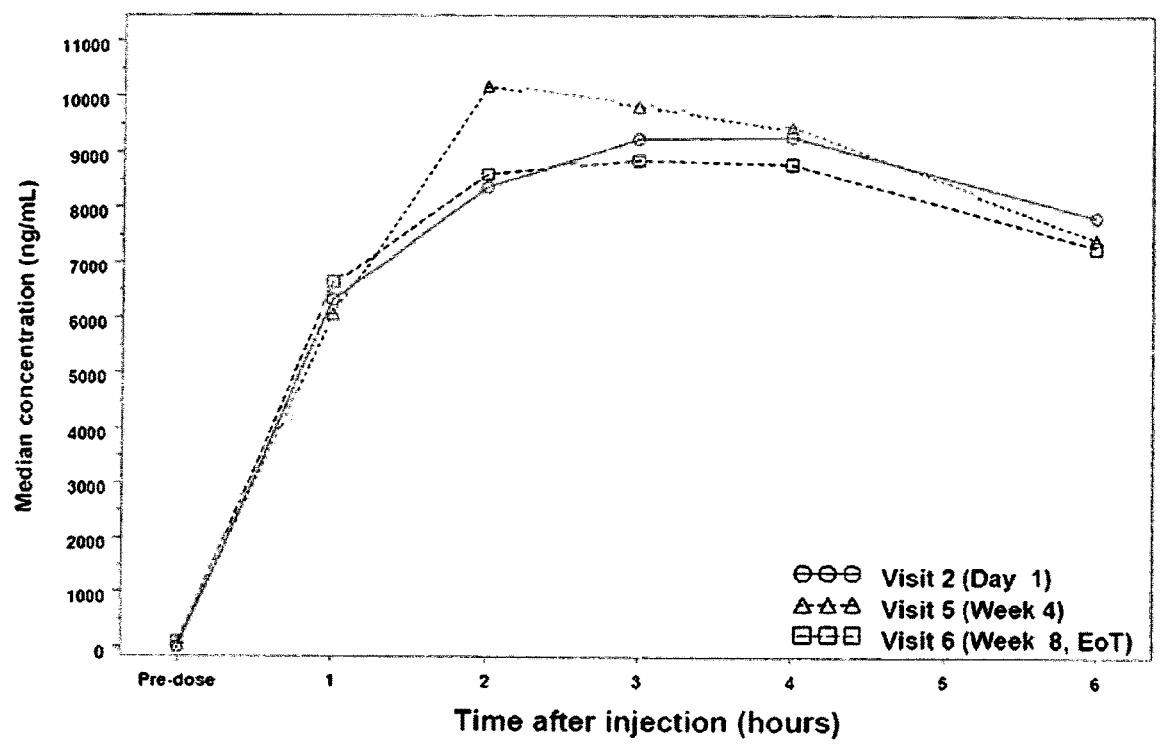

METHOD FOR REDUCING CIRCULATING LEUKOCYTES IN A HUMAN SUBJECT

CROSS-REFERENCE TO RELATED APPLICATIONS

This application is a continuation of U.S. patent application Ser. No. 13/823,101, filed Aug. 9, 2013, which is a U.S. National Phase under 35 U.S.C. §371 of International Application No. PCT/AU2011/001205, filed Sep. 19, 2011, which claims priority to the U.S. Provisional Patent Application No. 61/384,153, filed Sep. 17, 2010, each of which is hereby incorporated by reference in its entirety into this application.

SEQUENCE LISTING

A Sequence Listing is provided herewith as a text file, FBRIC67_002C1.txt created on Feb. 16, 2016 and having a size of 2.5 KB. The contents of the text file are incorporated by reference herein in their entirety.

FIELD OF THE INVENTION

The present disclosure provides methods for the mobilization of stem and/or progenitor cells. In one example, the present disclosure provides methods for the mobilization of hematopoietic stem and/or progenitor cells from the bone marrow to the peripheral blood.

BACKGROUND OF THE INVENTION

Hematopoietic stem cells can self-renew, differentiate to progenitor cells that give rise to the myeloid, erythroid, megakaryocytic, and lymphoid cell lineages in blood, mobilize out of the bone marrow into circulating blood, and undergo programmed cell death (apoptosis). Hematopoietic stem cells can be isolated from the blood or bone marrow.

Stem cells have commonly been characterized by their surface antigenic determinants. Such cell markers can be used to identify and isolate hematopoietic stem cells from the blood or bone marrow. The groups of cells thus isolated include some cells that are true, long-term self-renewing stem cells, some shorter-term progenitors, and some non-stem cells.

The classic source of hematopoietic stem cells is bone marrow. About 1 in every 10,000 cells in the marrow is a long-term, blood-forming stem cell; other cells present include stromal cells, stromal stem cells, blood progenitor cells, and mature and maturing white and red blood cells.

In recent years, the majority of autologous (where the donor and recipient are the same individual) and allogeneic (where the donor and recipient are different individuals) "bone marrow" transplants have actually been blood cells stem and progenitor cells drawn from peripheral circulation, not bone marrow. It is known that hematopoietic stem and progenitor cells migrate from bone marrow to blood in greater numbers by injecting the donor with for example, a cytokine, such as granulocyte-colony stimulating factor (G-CSF). The donor is typically injected with G-CSF a few days before the cell harvest. Of the cells collected, 5-20% are true hematopoietic stem cells.

There is a need for methods for mobilizing stem and/or progenitor cells from the bone marrow to the blood to facilitate harvest thereof.

SUMMARY OF THE INVENTION

Surprisingly, the present inventors have found that multipotent and/or oligopotent cells can be mobilized to the peripheral blood using an antisense compound that inhibits α4 integrin expression and/or VLA-4 and/or α4β7 integrin expression. Mobilization of multipotent and/or oligopotent cells is advantageous for subsequent successful engraftment, for example, hematopoietic reconstitution in patients receiving bone marrow ablative (myeloablative) doses of radiation and chemotherapy.

Accordingly, the present disclosure provides a method for mobilizing CD34 positive, α4 integrin positive, multipotent and/or oligopotent cells to the peripheral blood of a human subject, the method comprising administering to the subject an effective amount of an antisense compound to α4 integrin.

In one embodiment, the cells are mobilized from the bone marrow.

In a further embodiment, the cells are hematopoietic stem and/or progenitor cells.

In another embodiment, the cells are mesenchymal or endothelial stem and/or progenitor cells.

In one embodiment, the antisense compound is:

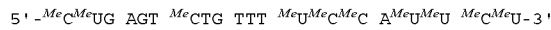

wherein,
a) each of the 19 internucleotide linkages of the oligonucleotide is an O,O-linked phosphorothioate diester;
b) the nucleotides at the positions 1 to 3 from the 5' end are 2'-O-(2-methoxyethyl) modified ribonucleosides;
c) the nucleotides at the positions 4 to 12 from the 5' end are 2'-deoxyribonucleosides;
d) the nucleotides at the positions 13 to 20 from the 5' end are 2'-O-(2-methoxyethyl) modified ribonucleosides; and
e) all cytosines are 5-methylcytosines ($^{Me}C$),
or a pharmaceutically acceptable salt thereof.

The present disclosure also provides a method for mobilizing CD34 positive, α4 integrin positive, multipotent and/or oligopotent cells to the peripheral blood of a subject, the method comprising administering to the subject an effective amount of antisense compound:

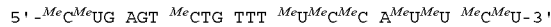

wherein,
a) each of the 19 internucleotide linkages of the oligonucleotide is an O,O-linked phosphorothioate diester;
b) the nucleotides at the positions 1 to 3 from the 5' end are 2'-O-(2-methoxyethyl) modified ribonucleosides;
c) the nucleotides at the positions 4 to 12 from the 5' end are 2'-deoxyribonucleosides;
d) the nucleotides at the positions 13 to 20 from the 5' end are 2'-O-(2-methoxyethyl) modified ribonucleosides; and
e) all cytosines are 5-methylcytosines ($^{Me}C$),
or a pharmaceutically acceptable salt thereof.

In one embodiment, cells are mobilized from the bone marrow.

In a further embodiment, the cells are hematopoietic stem and/or progenitor cells.

In another embodiment, the cells are mesenchymal or endothelial stem and/or progenitor cells.

In one embodiment, the methods of the disclosure comprise administering the antisense compound at least once per week, at least twice per week, at least three times per week, or at least four times per week.

In another embodiment, the methods of the disclosure comprise administering the antisense compound once daily, or every two days, three days or four days.

In another embodiment, the methods of the disclosure comprise administering 200, 400, 600, 800, 1000, 1200, 1400, 1600, 1800, 2000, 2200, 2400, 2600, 2800, 3000, 3200, or 3400 mg of the antisense compound per kilogram body weight over the course of the treatment.

In another embodiment, the methods of the disclosure comprise administering to 1600 mg of the antisense compound per kilogram body weight over the course of the treatment.

In another embodiment, the methods of the disclosure comprise administering the antisense compound subcutaneously.

In another embodiment, the methods of the disclosure comprise administering 6 mg of the antisense compound per Kg bodyweight as a single subcutaneous injection, or two subcutaneous injections.

In one embodiment, the methods of the disclosure further comprise administering a growth factor or analogue thereof, or a CXCR4 inhibitor.

In one embodiment, the growth factor is G-CSF, GM-CSF, SDF-1, or SCF.

In one embodiment, the growth factor or analogue thereof, or the CXCR4 inhibitor is administered prior to, subsequently, or concurrently with the antisense compound.

In one embodiment, the methods of the disclosure further comprise administering a growth factor and a CXCR4 inhibitor prior to, subsequently, or concurrently with the antisense compound.

In one embodiment, the methods of the disclosure further comprise administering low dose chemotherapy or an additional α4 integrin antagonist (for example, an anti-α4 integrin antibody) prior to, subsequently, or concurrently with the antisense compound.

In one embodiment, the methods of the disclosure further comprise harvesting the mobilized cells. In one example, peripheral blood of the subject is collected by apheresis.

In one embodiment, the cells are harvested at least 4 days after administration of the antisense compound.

In one embodiment, the methods of the disclosure further comprise monitoring the number of CD34 positive multipotent and/or oligopotent cells in the peripheral blood prior to harvesting the cells.

In one example, the cells are monitored by colony forming units. In another example, the cells are monitored by flow cytometry, by, for example, expression of one or more cell surface antigenic determinants.

In one embodiment, the methods of the disclosure further comprise monitoring the number of B cells, CD4$^+$ T cells, CD8$^+$ T cells, natural killer cells, monocytes, dendritic cells, platelets, neutrophils, eosinophils and/or basophils in the peripheral blood is monitored prior to harvesting the mobilized cells.

In one example, the cells are harvested following a reduction in the number of one or more of B cells, CD4$^+$ T cells, neutrophils, eosinophils and/or basophils.

In one embodiment, the methods of the disclosure further comprise monitoring the $C_{max}$ and/or $C_{trough}$ plasma levels of the antisense compound prior to harvesting the cells.

In one example, the $C_{trough}$ is between 20 to 45 ng/mL

In one embodiment, the subject is a mammal, preferably, a human.

The present disclosure also provides a method for the treatment of failure or dysfunction of normal blood cell production and maturation, hematopoietic malignancy, autoimmune disease, liver disease, or immunodeficiency, the method comprising administering cells harvested following mobilization according to the methods of the disclosure to a subject in need.

In one embodiment, the cells are allogeneic.

In another embodiment, cells are autologous.

Any embodiment herein shall be taken to apply mutatis mutandis to any other embodiment unless specifically stated otherwise.

The present invention is not to be limited in scope by the specific embodiments described herein, which are intended for the purpose of exemplification only. Functionally-equivalent products, compositions and methods are clearly within the scope of the invention, as described herein.

The invention is hereinafter described by way of the following non-limiting Examples and with reference to the accompanying figures.

BRIEF DESCRIPTION OF THE ACCOMPANYING DRAWINGS

FIG. 1. Pharmacokinetics data—median profiles of the human α4 integrin antisense compound (ATL1102) show no indication of accumulating peak or total plasma exposure levels from Day 1 to Week 8.

KEY TO THE SEQUENCE LISTING

SEQ ID NO:1 human α4 integrin antisense compound (ATL1102)
SEQ ID NO:2 murine α4 integrin antisense compound (ISIS348574).

DETAILED DESCRIPTION OF THE INVENTION

General Techniques and Selected Definitions

Unless specifically defined otherwise, all technical and scientific terms used herein shall be taken to have the same meaning as commonly understood by one of ordinary skill in the art (e.g., in cell culture, molecular genetics, immunology, immunohistochemistry, protein chemistry, and biochemistry).

Unless otherwise indicated, the recombinant protein, cell culture, and immunological techniques utilized in the present invention are standard procedures, well known to those skilled in the art. Such techniques are described and explained throughout the literature in sources such as, J. Perbal, A Practical Guide to Molecular Cloning, John Wiley and Sons (1984), J. Sambrook et al., Molecular Cloning: A Laboratory Manual, Cold Spring Harbour Laboratory Press (1989), T. A. Brown (editor), Essential Molecular Biology: A Practical Approach, Volumes 1 and 2, IRL Press (1991), D. M. Glover and B. D. Hames (editors), DNA Cloning: A Practical Approach, Volumes 1-4, IRL Press (1995 and 1996), F. M. Ausubel et al. (editors), Current Protocols in Molecular Biology, Greene Pub. Associates and Wiley-Interscience (1988, including all updates until present), E. Harlow and D. Lane (editors), Antibodies: A Laboratory Manual, Cold Spring Harbour Laboratory (1988), and J. E. Coligan et al. (editors), Current Protocols in Immunology, John Wiley and Sons (including all updates until present).

The term "and/or", for example, "X and/or Y" shall be understood to mean either "X and Y" or "X or Y" and shall be taken to provide explicit support for both meanings or for either meaning.

As used herein, "about" or "approximately" shall generally mean within 20%, more preferably within 10%, and even more preferably within 5%, of a given value or range.

Throughout this specification, or the word "comprise", or variations such as "comprises" or "comprising", will be understood to imply the inclusion of a stated element, integer or step, or group of elements, integers or steps, but not the exclusion of any other element, integer or step, or group of elements, integers or steps.

Throughout this specification, unless specifically stated otherwise or the context requires otherwise, reference to a single step, composition of matter, group of steps or group of compositions of matter shall be taken to encompass one and a plurality (i.e. one or more) of those steps, compositions of matter, groups of steps or group of compositions of matter.

The term "stem cells" as used herein refers to cells that have the capacity to self renew (i.e., go through numerous cycles of cell division while maintaining the undifferentiated state) and to differentiate into specialized cell types. In the strictest sense, stem cells can be either totipotent or pluripotent, although multipotent progenitor cells are often called stem cells and oligopotent, dualpotent or unipotent progenitor cells are sometimes referred to as stem cells. The presence of stem cells can be assessed, for example, by analysis (for example, flow cytometric analysis) of surface antigenic determinants. In one example, the stem cells are hematopoietic stem cells.

"Hematopoietic stem cells" can self renew and differentiate to give rise to all the blood cell types including myeloid (monocytes and macrophages, neutrophils, basophils, eosinophils, dendritic cells), erythroid (erythrocytes), megakaryocytic (platelets) and lymphoid lineages (T-cells, B-cells, NK-cells). Throughout differentiation, the hematopoietic stem cell first loses its self-renewal capacity, then loses lineage potential step by step as it commits to becoming a mature effector cell. Typically, a $Lin^-$, $c\text{-}Kit^+$, $SCA\text{-}1^+$, $Flk^{2-}$, $CD34^-$, $Slamf1^+$ murine cell is a hematopoietic stem cell. Such cells are typically detactable in 8 week old mice. Typically a $Lin^-$, $CD34^+$, $CD38^-$, $CD90^+$, $CD45RA^-$ human cell is a hematopoietic stem cell. Hematopoetic stem cells are sometimes referred to as pluripotent or multipotent stem and/or progenitor cells. In one embodiment, expression of CD34 is used to identify hematopoietic stem cells in peripheral blood isolated from human donors. This marker is also present on hematopoietic progenitor cells. The groups of cells thus isolated typically include some cells that are true, long-term self-renewing stem cells, some shorter term progenitors, and also contaminant near end and end stage blood cells.

The term "progenitor cells" as used herein refers to multipotent, oligopotent, dualpotent, or unipotent cells and includes hematopoietic, mesenchymal and endothelial progenitor cells. Common lymphoid progenitor (CLP) and common myeloid progenitor (CMP) cells are precursors of the lymphoid and myeloid compartments. These mature into cohorts of committed progenitor cells with progressively restricted differentiation potential, culminating in the non-replicating late stage precursors and end cells of the major hematopoietic lineages. CFU-GEMM cells are derived from CMP cells. CFU-GEMM cells have the potential to give rise to all blood cells except lymphocytes. CFU-GEMM cells give rise to CFU-GM and BFU-E cells. CFU-GEMM has high proliferative capacity compared with CFU-GM and BFU-E cells. However, CFU-GM and BFU-E cells are more prevalent. CLP cells give rise to T and B and other lymphocytes.

The presence of progenitor cells can be assessed by, for example, the ability of the cells in a sample to form colony-forming units of various types, including, for example, CFU-GEMM (colony-forming units, multipotent/oligopotent-granulocyte, erythrocyte, megakaryocyte, monocyte); CFU-GM (colony-forming units, dualpotent-granulocyte, macrophage); BFU-E (burst-forming units, unipotent-erythroid); HPP-CFC (high proliferative potential colony-forming cells). The development of in vitro clonogenic assays has defined subsets of progenitors of the myeloid lineages that appear to have restricted differentiation capacity. Conditions have been developed that support the in vitro formation of morphologically distinct colonies of hematopoietic cells (including red blood cells, granulocytes, macrophages, platelets, etc.) and non-hematopoietic cells (e.g., mesenchymal) by the clonal growth and maturation of progenitor cells. Specific formulations of different growth factors and other nutrients within the assay medium determine which type of progenitor colony develops within the culture system.

The presence of progenitor cells (including CLP populations) can be assessed by other analysis (for example, flow cytometric analysis) of surface antigenic determinants (Table I). Although CMP and CLP cells have antigenic determinant profiles that below may be categorized as oligopotent, they are often referred to in the literature as multipotent. The CFU-GEMM progenitor similarly profiles as oligopotent antigenically, but is often referred to in the literature as multipotent.

TABLE I

Exemplary surface antigenic determinant profiles of multipotent and oligopotent hematopoietic progenitor cells

|  | Mouse | Human |
| --- | --- | --- |
| Multipotent progenitors | $Lin^-$, $c\text{-}Kit^+$, $Sca\text{-}1^+$, $Flk^{2-}$, $CD34^+$, $Slamf1^+$<br>$Lin^-$, $c\text{-}Kit^+$, $Sca\text{-}1^+$, $Flk^{2-}$, $CD34^+$, $Slamf1^-$<br>$Lin^-$, $c\text{-}Kit^+$, $Sca\text{-}1^+$, $Flk^{2+}$, $CD34^+$, $Slamf1^-$ | $Lin^-$, $CD34^+$, $CD38^-$, $CD90^-$, $CD45RA^-$ |
| Oligopotent progenitors | $Lin^-$, $Flk^{2+}$, $IL7Ra^+$, $CD27^+$<br>$Lin^-$, $c\text{-}Kit^+$, $Sca\text{-}1^{-/low}$, $CD34^+$, $FcgR^{low}$<br>$Lin^-$, $c\text{-}Kit^+$, $SCA\text{-}1^-$, $CD34^-$, $FcgR^-$<br>$Lin^-$, $c\text{-}Kit^+$, $SCA\text{-}1^-$, $CD34^+$, $FcgR^+$ | $Lin^-$, $CD34^+$, $CD38^+$, $CD10^+$<br>$Lin^-$, $CD34^+$, $CD38^+$, $IL3Ra^{low}$, $CD45RA^-$<br>$Lin^-$, $CD34^+$, $CD38^+$, $IL3Ra^-$, $CD45RA^-$<br>$Lin^-$, $CD34^+$, $CD38^+$, $IL3Ra^+$, $CD45RA^-$ |

In one embodiment, the total number of non stem cell CFU-progenitors is a predictor of stem cell recovery, and platelet or neutrophil recovery.

The term "totipotent cells" (also known as omnipotent) as used herein refers to cells that can differentiate into embryonic and extraembryonic cell types. Such cells can construct a complete, viable, organism. These cells are produced from the fusion of an egg and sperm cell. Cells produced by the first few divisions of the fertilized egg are also totipotent.

The term "pluripotent cells" as used herein refers to cells that are the descendants of totipotent cells and can differentiate into nearly all cells (i.e., cells derived from any of the three germ layers).

The term "multipotent cells" as used herein refers to cells that can differentiate into a number of cells, but only those of a closely related family of cells and includes hematopoietic stem cells.

The term "oligopotent cells" as used herein refers to cells that can differentiate into only a few cells, and includes lymphoid or myeloid progenitor cells, for example, CMP, CLP and CFU-GEMM cells.

The term "dualpotent cells" as used herein refers to cells that can differentiate into only two cell types, for example, CFU-GM cells.

The term "unipotent cells" refers to cells that can differentiate into only one cell type, their own, but have the property of self-renewal which distinguishes them from non-stem/progenitor cells, for example, BFU-E cells.

In the context of cell ontogeny, the adjective "differentiated" is a relative term. A "differentiated cell" is a cell that has progressed further down the developmental pathway than the cell it is being compared with.

The term "mobilization" as used herein refers to movement of stem and/or progenitor cells from any tissue source, for example, bone marrow to the peripheral blood and results in an increase in the population of stem and/or progenitor cells or specific subpopulations of cells in peripheral blood.

The term "antisense compound" as used herein refers to an oligomeric compound that hybridizes to a nucleic acid molecule encoding the α4 integrin chain of VLA-4 and/or α4β7 integrin to effect mobilization of stem and/or progenitor cells. The α4 integrin chain in humans is CD49d. The antisense compound may interfere with expression of CD49d, β1 integrin and/or β7 integrin.

The term "nucleic acid molecule encoding α4 integrin" as used herein is interchangeable with "target nucleic acid" and encompasses DNA encoding the α4 integrin chain of VLA-4 or α4β7 integrin, RNA (including pre-mRNA and mRNA or portions thereof) transcribed from such DNA, and further, cDNA derived from such RNA.

The term "VLA-4" as used herein refers to a heterodimer of an α4 integrin and a β1 integrin. VLA-4 is expressed at substantial levels on normal peripheral blood B and T cells, thymocytes, monocytes, and other cells, as well as on hematopoietic stem and progenitor cells. VLA-4 is also expressed on mesenchymal and endothelial progenitor cells and mesenchymal stem cells and potentially endothelial stem cells. Ligands for VLA-4 include vascular cell adhesion molecule-1 (VCAM-1) and CS-1, an alternately spliced domain within the Hep II region of fibronectin.

The term "α4β7 integrin" as used herein refers to a hetereodimer of an α4 integrin and a β7 integrin. α4β7 integrin identifies a subset of memory T cells with a tropism for the intestinal tract. α4β7 integrin and is also expressed on a subset of mast, lymphocyte and NK progenitor cells. α4β7 integrin is expressed on some stem and progenitor cells. Ligands for α4β7 integrin include MAdCam-1 and VCAM-1.

The term "G-CSF polypeptide" or "G-CSF" as used herein refers to a naturally occurring human and heterologous species G-CSF, recombinantly produced G-CSF, the expression product consisting of either 174 or 177 amino acids, or fragments, analogs, variants, or derivatives thereof as reported, for example, in Kuga et al., 1989; Lu et al., 1989; U.S. Pat. No. 4,810,643, U.S. Pat. No. 4,904,584, U.S. Pat. No. 5,104,651, U.S. Pat. No. 5,214,132, U.S. Pat. No. 5,218,092, U.S. Pat. No. 5,362,853, U.S. Pat. No. 5,606,024, U.S. Pat. No. 5,824,778, U.S. Pat. No. 5,824,784, U.S. Pat. No. 6,017,876, U.S. Pat. No. 6,166,183, U.S. Pat. No. 6,261,550, US 2003/0064922, EP 0 335423, EP 0 272703, EP 0 459630, EP 0 256843, EP 0 243153, WO 9102874, AU-A-10948/92 and AU-A-76380/91. Included are chemically modified G-CSFs, see for example, those reported in WO 9012874, EP and EP 0 335423. See also, WO 03006501; WO 03030821, WO 0151510, WO 9611953, WO 9521629, WO 9420069, WO 9315211, WO 9305169, JP 04164098, WO 9206116, WO 9204455, EP 0 473268, EP 0 456200, WO 9111520, WO 9105798, WO 9006952, WO 8910932, WO 8905824, WO 9118911, and EP 0 370205. Also encompassed herein are all forms of G-CSF, such as Albugranin™, Neuulasta™, Neupogen™, and Granocyte™.

Antisense Compounds to α4 Integrin

The methods of the present disclosure rely on the use of an antisense compound to α4 integrin for the mobilization of stem and/or progenitor cells. Such antisense compounds are targeted to nucleic acids encoding the α4 integrin chain of VLA-4 or α4b7. Preferably, the antisense compound is an oligonucleotide. However, other oligomeric antisense compounds, including but not limited to oligonucleotide mimetics are contemplated.

Hybridization of an antisense compound with its target nucleic acid is generally referred to as "antisense". Hybridization of the antisense compound with its target nucleic acid inhibits the function of the target nucleic acid. Such "antisense inhibition" is typically based upon hydrogen bonding-based hybridization of the antisense compound to the target nucleic acid such that the target nucleic acid is cleaved, degraded, or otherwise rendered inoperable. The functions of target DNA to be interfered with can include replication and transcription. Replication and transcription, for example, can be from an endogenous cellular template, a vector, a plasmid construct or otherwise. The functions of RNA to be interfered with can include functions such as translocation of the RNA to a site of protein translation, translocation of the RNA to sites within the cell which are distant from the site of RNA synthesis, translation of protein from the RNA, splicing of the RNA to yield one or more RNA species, and catalytic activity or complex formation involving the RNA which may be engaged in or facilitated by the RNA.

"Hybridization" as used herein means pairing of complementary bases of the oligonucleotide and target nucleic acid. Base pairing typically involves hydrogen bonding, which may be Watson-Crick, Hoogsteen or reversed Hoogsteen hydrogen bonding, between complementary nucleoside or nucleotide bases (nucleobases). Guanine (G) and cytosine (C) are examples of complementary nucleobases which pair through the formation of 3 hydrogen bonds. Adenine (A) and thymine (T) are examples of complementary nucleobases which pair through the formation of 2 hydrogen bonds. Hybridization can occur under varying circumstances.

A "nucleoside" is a base-sugar combination. The base portion of the nucleoside is normally a heterocyclic base. The two most common classes of such heterocyclic bases are the purines and the pyrimidines. "Nucleotides" are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar.

"Specifically hybridizable" and "complementary" are terms which are used to indicate a sufficient degree of complementarity such that stable and specific binding occurs between the antisense compound and target nucleic acid. It is understood that the antisense compound need not be 100% complementary to its target nucleic acid sequence to be specifically hybridizable. An antisense compound is specifically hybridizable when binding of the antisense compound to the target nucleic acid interferes with the normal function of the target molecule to cause a loss of activity, and there is a sufficient degree of complementarity to avoid non-specific binding of the antisense compound to non-target sequences under conditions in which specific binding is desired, for example, under physiological conditions in the case of therapeutic treatment.

The term "stringent hybridization conditions" or "stringent conditions" as used herein refers to conditions under which the antisense compound will hybridize to its target sequence, but to a minimal number of other sequences. Stringent conditions are sequence-dependent and will be different in different circumstances. Stringent condition under which the antisense compound hybridizes to a target sequence is determined by the nature and composition of the antisense compound and the assays in which it is being investigated.

"Complementary" as used herein, refers to the capacity for precise pairing between a nucleobase of the antisense compound and the target nucleic acid. For example, if a nucleobase at a certain position of the antisense compound is capable of hydrogen bonding with a nucleobase at a certain position of the target nucleic acid, then the position of hydrogen bonding between the antisense compound and the target nucleic acid is considered to be a complementary position. The antisense compound may hybridize over one or more segments, such that intervening or adjacent segments are not involved in the hybridization event (e.g., a loop structure or hairpin structure). In one embodiment, the antisense compound comprises at least 70% sequence complementarity to a target region within the target nucleic acid. For example, an antisense compound in which 18 of 20 nucleobases are complementary to a target region within the target nucleic acid, and would therefore specifically hybridize, would represent 90% complementarity. In this example, the remaining noncomplementary nucleobases may be clustered or interspersed with complementary nucleobases and need not be contiguous to each other, or to complementary nucleobases. As such, an antisense compound which is 18 nucleobases in length having 4 non-complementary nucleobases which are flanked by 2 regions of complete complementarity with the target nucleic acid would have 77.8% overall complementarity with the target nucleic acid and would thus, fall within the scope of the present disclosure. Percent complementarity of an antisense compound with a region of a target nucleic acid can be determined routinely using BLAST programs (basic local alignment search tools) and PowerBLAST programs known in the art (Altschul et al., 1990; Zhang and Madden, 1997).

Antisense Oligonucleotides

The present disclosure provides antisense oligonucleotides for inhibiting expression of α4 integrin, and/or VLA-4 and/or α4β7 integrin. Such antisense oligonucleotides are targeted to nucleic acids encoding the α4 integrin chain of VLA-4 or α4b7.

The term "inhibits" as used herein means any measurable decrease (e.g., 10%, 20%, 50%, 90%, or 100%) in VLA-4 or α4β7 integrin expression.

As used herein, the term "oligonucleotide" refers to an oligomer or polymer of RNA or DNA or mimetics, chimeras, analogs and homologs thereof. This term includes oligonucleotides composed of naturally occurring nucleobases, sugars and covalent internucleoside (backbone) linkages, as well as oligonucleotides having non-naturally occurring portions which function similarly. Such modified or substituted oligonucleotides are often preferred over native forms because of desirable properties such as, for example, enhanced cellular uptake, enhanced affinity for the target nucleic acid and increased stability in the presence of nucleases.

In forming oligonucleotides, phosphate groups covalently link adjacent nucleosides to one another to form a linear polymeric compound. In turn, the respective ends of this linear polymeric compound can be further joined to form a circular compound; however, linear compounds are generally preferred. In addition, linear compounds may have internal nucleobase complementarity and may therefore fold in a manner so as to produce a fully or partially double-stranded compound. With regard to oligonucleotides, the phosphate groups are commonly referred to as forming the internucleoside backbone of the oligonucleotide. The normal linkage or backbone of RNA and DNA is a 3' to 5' phosphodiester linkage.

Antisense oligonucleotides of the disclosure include, for example, ribozymes, siRNA, external guide sequence (EGS) oligonucleotides, alternate splicers, primers, probes, and other oligonucleotides which hybridize to at least a portion of the target nucleic acid.

Antisense oligonucleotides of the disclosure may be administered in the form of single-stranded, double-stranded, circular or hairpin and may contain structural elements such as internal or terminal bulges or loops. Once administered, the antisense oligonucleotides may elicit the action of one or more enzymes or structural proteins to effect modification of the target nucleic acid.

One non-limiting example of such an enzyme is RNAse H, a cellular endonuclease which cleaves the RNA strand of an RNA:DNA duplex. It is known in the art that single-stranded antisense compounds which are "DNA-like" elicit RNAse H. Activation of RNase H therefore results in cleavage of the RNA target, thereby greatly enhancing the efficiency of oligonucleotide-mediated inhibition of gene expression. Similar roles have been postulated for other ribonucleases, such as those in the RNase III and ribonuclease L family of enzymes.

The introduction of double-stranded RNA (dsRNA) molecules, has been shown to induce potent and specific antisense-mediated reduction of the function of a gene or its associated gene products. This phenomenon occurs in both plants and animals and is believed to have an evolutionary connection to viral defense and transposon silencing.

The first evidence that dsRNA could lead to gene silencing in animals came in 1995 from work in the nematode, *Caenorhabditis elegans* (Guo and Kempheus, 1995). Montgomery et al. (1998) have shown that the primary interference effects of dsRNA are posttranscriptional. The posttranscriptional antisense mechanism defined in *Caenorhabditis elegans* resulting from exposure to double-stranded RNA (dsRNA) has since been designated RNA interference (RNAi). This term has been generalized to mean antisense-mediated gene silencing involving the introduction of dsRNA leading to the sequence-specific reduction of endogenous targeted mRNA levels (Fire et al., 1998). Recently, it has been shown that it is, in fact, the single-stranded RNA oligomers of antisense polarity of the dsRNAs which are the potent inducers of RNAi (Tijsterman et al., 2002).

A person having ordinary skill in the art could, without undue experimentation, identify antisense oligonucleotides useful in the methods of the present disclosure.

Modified Internucleoside Linkages (Backbones)

Antisense compounds of the present disclosure include oligonucleotides having modified backbones or non-natural internucleoside linkages. Oligonucleotides having modified backbones include those that retain a phosphorus atom in the backbone and those that do not have a phosphorus atom in the backbone.

Modified oligonucleotide backbones containing a phosphorus atom therein include, for example, phosphorothioates, chiral phosphorothioates, phosphorodithioates, phosphotriesters, aminoalkylphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates, and boranophosphates having normal 3'-5' linkages, 2'-5' linked analogs of these, and those having inverted polarity wherein one or more internucleotide linkages is a 3' to 3', 5' to 5' or 2' to 2' linkage.

Oligonucleotides having inverted polarity comprise a single 3' to 3' linkage at the 3'-most internucleotide linkage, that is, a single inverted nucleoside residue which may be abasic (the nucleobase is missing or has a hydroxyl group in place thereof). Various salts, mixed salts and free acid forms are also included.

Representative United States patents that teach the preparation of the above phosphorus-containing linkages include, but are not limited to, U.S. Pat. No. 3,687,808, U.S. Pat. No. 4,469,863, U.S. Pat. No. 4,476,301, U.S. Pat. No. 5,023,243, U.S. Pat. No. 5,177,196, U.S. Pat. No. 5,188,897, U.S. Pat. No. 5,264,423, U.S. Pat. No. 5,276,019, U.S. Pat. No. 5,278,302, U.S. Pat. No. 5,286,717, U.S. Pat. No. 5,321,131, U.S. Pat. No. 5,399,676, U.S. Pat. No. 5,405,939, U.S. Pat. No. 5,453,496, U.S. Pat. No. 5,455,233, U.S. Pat. No. 5,466,677, U.S. Pat. No. 5,476,925, U.S. Pat. No. 5,519,126, U.S. Pat. No. 5,536,821, U.S. Pat. No. 5,541,306, U.S. Pat. No. 5,550,111, U.S. Pat. No. 5,563,253, U.S. Pat. No. 5,571,799, U.S. Pat. No. 5,587,361, U.S. Pat. No. 5,194,599, U.S. Pat. No. 5,565,555, U.S. Pat. No. 5,527,899, U.S. Pat. No. 5,721,218, U.S. Pat. No. 5,672,697 and U.S. Pat. No. 5,625,050.

Modified oligonucleotide backbones that do not include a phosphorus atom therein include, for example, backbones formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative United States patents that teach the preparation of the above oligonucleotides include, but are not limited to, U.S. Pat. No. 5,034,506, U.S. Pat. No. 5,166,315, U.S. Pat. No. 5,185,444, U.S. Pat. No. 5,214,134, U.S. Pat. No. 5,216,141, U.S. Pat. No. 5,235,033, U.S. Pat. No. 5,264,562, U.S. Pat. No. 5,264,564, U.S. Pat. No. 5,405,938, U.S. Pat. No. 5,434,257, U.S. Pat. No. 5,466,677, U.S. Pat. No. 5,470,967, U.S. Pat. No. 5,489,677, U.S. Pat. No. 5,541,307, U.S. Pat. No. 5,561,225, U.S. Pat. No. 5,596,086, U.S. Pat. No. 5,602,240, U.S. Pat. No. 5,610,289, U.S. Pat. No. 5,602,240, U.S. Pat. No. 5,608,046, U.S. Pat. No. 5,610,289, U.S. Pat. No. 5,618,704, U.S. Pat. No. 5,623,070, U.S. Pat. No. 5,663,312, U.S. Pat. No. 5,633,360, U.S. Pat. No. 5,677,437, U.S. Pat. No. 5,792,608, U.S. Pat. No. 5,646,269 and U.S. Pat. No. 5,677,439.

Modified Sugar and Internucleoside Linkages

Antisense compounds of the present disclosure include oligonucleotide mimetics where both the sugar and the internucleoside linkage (i.e. the backbone), of the nucleotide units are replaced with novel groups. The nucleobase units are maintained for hybridization with the target nucleic acid.

An oligonucleotide mimetic that has been shown to have excellent hybridization properties is referred to as a peptide nucleic acid (PNA). In PNA compounds, the sugar-backbone of an oligonucleotide is replaced with an amide containing backbone, in particular, an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. No. 5,539,082, U.S. Pat. No. 5,714,331, and U.S. Pat. No. 5,719,262. Further teaching of PNA compounds can be found in Nielsen et al., 1991.

The antisense compounds of the present disclosure also include oligonucleotides with phosphorothioate backbones and oligonucleotides with heteroatom backbones, for example, $-CH_2-NH-O-CH_2-$, $-CH_2-N(CH_3)-O-CH_2-$ [known as a methylene (methylimino) or MMI backbone], $-CH_2-O-N(CH_3)-CH_2-$, $-CH_2-N(CH_3)-N(CH_3)-CH_2-$ and $-O-N(CH_3)-CH_2-CH_2-$ [wherein the native phosphodiester backbone is represented as $-O-P-O-CH_2-$] of U.S. Pat. No. 5,489,677, and the amide backbones of U.S. Pat. No. 5,602,240.

The antisense compounds of the present disclosure also include oligonucleotides having morpholino backbone structures of U.S. Pat. No. 5,034,506.

Modified Sugars

Antisense compounds of the present disclosure include oligonucleotides having one or more substituted sugar moieties.

Examples include oligonucleotides comprising one of the following at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl.

In one embodiment, the oligonucleotide comprises one of the following at the 2' position: $O[(CH_2)_nO]_mCH_3$, $O(CH_2)_nOCH_3$, $O(CH_2)_nNH_2$, $O(CH_2)_nCH_3$, $O(CH_2)_nONH_2$, and $O(CH_2)_nON[(CH_2)_nCH_3]_2$, where n and m are from 1 to about 10.

Further examples include of modified oligonucleotides include oligonucleotides comprising one of the following at the 2' position: $C_1$ to $C_{10}$ lower alkyl, substituted lower alkyl, alkenyl, alkynyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties.

In one embodiment, the modification includes 2'-methoxyethoxy (2'-O—$CH_2CH_2OCH_3$ (also known as 2'-O-(2-methoxyethyl) or 2'-MOE) (Martin et al., 1995), that is, an alkoxyalkoxy group. In a further embodiment, the modification includes 2'-dimethylaminooxyethoxy, that is, a $O(CH_2)_2ON(CH_3)_2$ group (also known as 2'-DMAOE), or 2'-dimethylaminoethoxyethoxy (also known in the art as 2'-O-dimethyl-amino-ethoxy-ethyl or 2'-DMAEOE), that is, 2'-O—$CH_2$—O—$CH_2$—$N(CH_3)_2$.

Other modifications include 2'-methoxy (2'-O—$CH_3$), 2'-aminopropoxy (2'-OCH_2CH_2CH_2NH_2), 2'-allyl (2'-$CH_2$—CH=$CH_2$), 2'-O-allyl (2'-O—$CH_2$—CH=$CH_2$) and 2'-fluoro (2'-F). The 2'-modification may be in the arabino (up) position or ribo (down) position. In one embodiment a 2'-arabino modification is 2'-F.

Similar modifications may also be made at other positions on the oligonucleotide, particularly the 3' position of the sugar on the 3' terminal nucleotide or in 2'-5' linked oligonucleotides and the 5' position of the 5' terminal nucleotide.

Oligonucleotides may also have sugar mimetics, such as cyclobutyl moieties in place of the pentofuranosyl sugar.

Representative United States patents that teach the preparation of such modified sugar structures include, but are not limited to, U.S. Pat. No. 4,981,957, U.S. Pat. No. 5,118,800, U.S. Pat. No. 5,319,080, U.S. Pat. No. 5,359,044, U.S. Pat. No. 5,393,878, U.S. Pat. No. 5,446,137, U.S. Pat. No. 5,466,786, U.S. Pat. No. 5,514,785, U.S. Pat. No. 5,519,134, U.S. Pat. No. 5,567,811, U.S. Pat. No. 5,576,427, U.S. Pat. No. 5,591,722, U.S. Pat. No. 5,597,909, U.S. Pat. No. 5,610,300, U.S. Pat. No. 5,627,053, U.S. Pat. No. 5,639,873, U.S. Pat. No. 5,646,265, U.S. Pat. No. 5,658,873, U.S. Pat. No. 5,670,633, U.S. Pat. No. 5,792,747, and U.S. Pat. No. 5,700,920.

A further modification of the sugar includes Locked Nucleic Acids (LNAs) in which the 2'-hydroxyl group is linked to the 3' or 4' carbon atom of the sugar ring, thereby forming a bicyclic sugar moiety. In one embodiment, the linkage is a methylene ($-CH_2-$)$_n$ group bridging the 2' oxygen atom and the 4' carbon atom, wherein n is 1 or 2. LNAs and preparation thereof are described in WO 98/39352 and WO 99/14226.

Natural and Modified Nucleobases

Antisense compounds of the present disclosure include oligonucleotides having nucleobase modifications or substitutions. As used herein, "unmodified" or "natural" nucleobases include the purine bases adenine (A) and guanine (G), and the pyrimidine bases thymine (T), cytosine (C) and uracil (U).

Modified nucleobases include other synthetic and natural nucleobases such as, for example, 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl ($-C\equiv C-CH_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine.

Further modified nucleobases include tricyclic pyrimidines, such as phenoxazine cytidine(1H-pyrimido[5,4-b][1,4]benzoxazin-2(3H)-one), phenothiazine cytidine (1H-pyrimido[5,4-b][1,4]benzothiazin-2(3H)-one), G-clamps such as, for example, a substituted phenoxazine cytidine (e.g., 9-(2-aminoethoxy)-H-pyrimido[5,4-b][1,4]benzoxazin-2 (3H)-one), carbazole cytidine (2H-pyrimido[4,5-b]indol-2-one), pyridoindole cytidine (H-pyrido[3',2':4,5]pyrrolo[2,3-d]pyrimidin-2-one).

Modified nucleobases may also include those in which the purine or pyrimidine base is replaced with other heterocycles, for example, 7-deaza-adenine, 7-deazaguanosine, 2-aminopyridine and 2-pyridone. Further nucleobases include those disclosed in U.S. Pat. No. 3,687,808, those disclosed in J. I. Kroschwitz (editor), The Concise Encyclopedia of Polymer Science and Engineering, pages 858-859, John Wiley and Sons (1990), those disclosed by Englisch et al. (1991), and those disclosed by Y. S. Sanghvi, Chapter 15: Antisense Research and Applications, pages 289-302, S. T. Crooke, B. Lebleu (editors), CRC Press, 1993.

Certain of these nucleobases are particularly useful for increasing the binding affinity of the oligonucleotide. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. In one embodiment, these nucleobase substitutions are combined with 2'-O-methoxyethyl sugar modifications.

Representative United States patents that teach the preparation of certain of the above noted modified nucleobases as well as other modified nucleobases include, but are not limited to, U.S. Pat. No. 3,687,808, U.S. Pat. No. 4,845,205, U.S. Pat. No. 5,130,302, U.S. Pat. No. 5,134,066, U.S. Pat. No. 5,175,273, U.S. Pat. No. 5,367,066, U.S. Pat. No. 5,432,272, U.S. Pat. No. 5,457,187, U.S. Pat. No. 5,459,255, U.S. Pat. No. 5,484,908, U.S. Pat. No. 5,502,177, U.S. Pat. No. 5,525,711, U.S. Pat. No. 5,552,540, U.S. Pat. No. 5,587,469, U.S. Pat. No. 5,594,121, U.S. Pat. No. 5,596,091, U.S. Pat. No. 5,614,617, U.S. Pat. No. 5,645,985, U.S. Pat. No. 5,830,653, U.S. Pat. No. 5,763,588, U.S. Pat. No. 6,005,096, U.S. Pat. No. 5,681,941 and U.S. Pat. No. 5,750,692.

Conjugates

Antisense compounds of the present disclosure may be conjugated to one or more moieties or groups which enhance the activity, cellular distribution or cellular uptake of the antisense compound.

These moieties or groups may be covalently bound to functional groups such as primary or secondary hydroxyl groups.

Exemplary moieties or groups include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugate groups include cholesterols, lipids, phospholipids, biotin, phenazine, folate, phenanthridine, anthraquinone, acridine, fluoresceins, rhodamines, coumarins and dyes.

Moieties or groups that enhance the pharmacodynamic properties include those that improve uptake, enhance resistance to degradation, and/or strengthen sequence-specific hybridization with the target nucleic acid.

Moieties or groups that enhance the pharmacokinetic properties include those that improve uptake, distribution, metabolism or excretion of the compounds of the present disclosure.

Representative moieties or groups are disclosed in PCT/US92/09196 and U.S. Pat. No. 6,287,860.

Moieties or groups include but are not limited to lipid moieties such as a cholesterol moiety, cholic acid, a thioether, for example, hexyl-S-tritylthiol, a thiocholesterol, an aliphatic chain, for example, dodecandiol or undecyl residues, a phospholipid, for example, di-hexadecyl-rac-glycerol or triethylammonium 1,2-di-O-hexadecyl-rac-glycero-3-H-phosphonate, a polyamine or a polyethylene glycol chain, or adamantane acetic acid, a palmityl moiety, or an octadecylamine or hexylamino-carbonyl-oxycholesterol moiety.

Antisense compounds of the present disclosure may also be conjugated to active drug substances.

Oligonucleotide-drug conjugates and their preparation are described in U.S. Ser. No. 09/334,130.

Representative United States patents that teach the preparation of such conjugates include, but are not limited to, U.S. Pat. No. 4,828,979, U.S. Pat. No. 4,948,882, U.S. Pat. No. 5,218,105, U.S. Pat. No. 5,525,465, U.S. Pat. No. 5,541,313, U.S. Pat. No. 5,545,730, U.S. Pat. No. 5,552,538, U.S. Pat. No. 5,578,717, U.S. Pat. No. 5,580,731, U.S. Pat. No. 5,580,731, U.S. Pat. No. 5,591,584, U.S. Pat. No. 5,109,124, U.S. Pat. No. 5,118,802, U.S. Pat. No. 5,138,045, U.S. Pat. No. 5,414,077, U.S. Pat. No. 5,486,603, U.S. Pat. No. 5,512,439, U.S. Pat. No. 5,578,718, U.S. Pat. No. 5,608,046, U.S. Pat. No. 4,587,044, U.S. Pat. No. 4,605,735, U.S. Pat. No. 4,667,025, U.S. Pat. No. 4,762,779, U.S. Pat. No. 4,789,737, U.S. Pat. No. 4,824,941, U.S. Pat. No. 4,835,263, U.S. Pat. No. 4,876,335, U.S. Pat. No. 4,904,582, U.S. Pat. No. 4,958,013, U.S. Pat. No. 5,082,830, U.S. Pat. No. 5,112,963, U.S. Pat. No. 5,214,136, U.S. Pat. No. 5,082,830, U.S. Pat. No. 5,112,963, U.S. Pat. No. 5,214,136, U.S. Pat. No. 5,245,022, U.S. Pat. No. 5,254,469, U.S. Pat. No. 5,258,506, U.S. Pat. No. 5,262,536, U.S. Pat. No. 5,272,250, U.S. Pat. No. 5,292,873, U.S. Pat. No. 5,317,098, U.S. Pat. No. 5,371,241, U.S. Pat. No. 5,391,723, U.S. Pat. No. 5,416,203, U.S. Pat. No. 5,451,463, U.S. Pat. No. 5,510,475, U.S. Pat. No. 5,512,667, U.S. Pat. No. 5,514,785, U.S. Pat. No. 5,565,552, U.S. Pat. No. 5,567,810, U.S. Pat. No. 5,574,142, U.S. Pat. No. 5,585,481, U.S. Pat. No. 5,587,371, U.S. Pat. No. 5,595,726, U.S. Pat. No. 5,597,696, U.S. Pat. No. 5,599,923, U.S. Pat. No. 5,599,928 and U.S. Pat. No. 5,688,941.

Chimeric Compounds

As would be appreciated by those skilled in the art, it is not necessary for all positions in a given compound to be uniformly modified and in fact, more than one of the aforementioned modifications may be incorporated in a single oligonucleotide or even at a single nucleoside within an oligonucleotide.

Antisense compounds of the disclosure include chimeric oligonucleotides. "Chimeric oligonucleotides" contain two or more chemically distinct regions, each made up of at least one monomer unit, that is, a nucleotide in the case of an oligonucleotide compound. These oligonucleotides typically contain at least one wherein the oligonucleotide is modified so as to confer upon the oligonucleotide increased resistance to nuclease degradation, increased cellular uptake, increased stability and/or increased binding affinity for the target nucleic acid. An additional region of the oligonucleotide may serve as a substrate for enzymes capable of cleaving RNA:DNA or RNA:RNA hybrids. By way of example, RNAse H is a cellular endonuclease which cleaves the RNA strand of an RNA:DNA duplex. Activation of RNase H, therefore, results in cleavage of the RNA target, thereby greatly enhancing the efficiency of oligonucleotide-mediated inhibition of gene expression. The cleavage of RNA:RNA hybrids can, in like fashion, be accomplished through the actions of endoribonucleases, such as RNAseL which cleaves both cellular and viral RNA. Cleavage of the RNA target can be routinely detected by gel electrophoresis and if necessary, associated nucleic acid hybridization techniques known in the art.

Chimeric antisense compounds of the disclosure may be formed as composite structures of two or more oligonucleotides, modified oligonucleotides, and/or oligonucleotide mimetics. Such compounds have also been referred to in the art as hybrids or gapmers.

Representative United States patents that teach the preparation of such hybrid structures include, but are not limited to, U.S. Pat. No. 5,013,830, U.S. Pat. No. 5,149,797, U.S. Pat. No. 5,220,007, U.S. Pat. No. 5,256,775, U.S. Pat. No. 5,366,878, U.S. Pat. No. 5,403,711, U.S. Pat. No. 5,491,133, U.S. Pat. No. 5,565,350, U.S. Pat. No. 5,623,065, U.S. Pat. No. 5,652,355, U.S. Pat. No. 5,652,356, and U.S. Pat. No. 5,700,922.

Exemplary Oligonucleotide

In one embodiment, the antisense compound is a second generation phosphorothioate backbone 2'-MOE-modified chimeric oligonucleotide gapmer designed to hybridize to the 3'-untranslated region of VLA-4 mRNA. The oligonucleotide selectively inhibits VLA-4 expression in both primary human cells and in several human cell lines by hybridizing to RNA encoding CD49, which is the α4 integrin subunit of VLA-4 and α4β7 integrin.

The oligonucleotide is the 19-sodium salt of a 3'→5' phosphorothioate oligonucleotide 20mer also referred as a 3-9-8 MOE gapmer having a molecular weight of 7230 Daltons, in which the nucleotides at positions 1 to 3 from the 5' end are 2'-O-(2-methoxyethyl) (2'MOE) modified ribonucleosides (2'-O-(2-methoxyethyl ribose); the nucleotides at positions 4 to 12 from the 5' end are 2'-deoxyribonucleosides of which all cytosines are 5-methylcytosines; the nucleotides at positions 13 to 20 from the 5' end are 2'-O-(2-methoxyethyl) modified ribonucleosides.

The sequence of the oligonucleotide is:

5'-$^{Me}C^{Me}UG$ AGT $^{Me}CTG$ TTT $^{Me}U^{Me}C^{Me}C$ A$^{Me}U^{Me}U$ $^{Me}C^{Me}U$-3'.

The empirical formula of the oligonucleotide is:
$C_{233}H_{327}N_{60}O_{129}P_{19}S_{19}Na_{19}$.

All uracils are 5-methyluracils ($^{Me}U$). Typically, the oligonucleotide is synthesized using 2-methoxyethyl modified thymidines not 5-methyluracils.

All pyrimidines are C5 methylated (i.e., U, T, C are C5 methylated).

The sequence of the oligonucleotide may be named by accepted oligonucleotide nomenclature, showing each O—O linked phosphorothioate internucleotide linkage:

2'-O-methoxyethyl-5-methylcytidylyl-(3'→5'O,O-phosphorothioyl)-2'-O-methoxyethyl-5-methyluridylyl-(3'→5' O,O-phosphorothioyl)-2'-O-methoxyethylguanosylyl-(3'→5' O,O-phosphorothioyl)-2'-O-deoxyadenosylyl-(3'→5' O,O-phosphorothioyl)-2'-O-deoxyguanosylyl-(3'→5' O,O-phosphorothioyl)-thymidylyl-(3'→5' O,O-phosphorothioyl)-2'-deoxy-5-methylcytidylyl-(3'→5'O,O-phosphorothioyl)-thymidylyl-(3'→5' O,O-phosphorothioyl)-2'-deoxyguanosylyl-(3'→5' O,O-phosphorothioyl)-thymidylyl-(3'→5' O,O-phosphorothioyl)-thymidylyl-(3'→5' O,O-phosphorothioyl)-thymidylyl-(3'→5' O,O-phosphorothioyl)-2'-O-methoxyethyl-5-methyluridylyl-(3→5' O,O-phosphorothioyl)-2'-methoxyethyl-5-methylcytidylyl-(3'→5' O,O-phosphorothioyl)-2'-methoxyethyl-5-methylcytidylyl-(3'→5' O,O-phosphorothioyl)-2'-O-methoxyethyl-5-adenosylyl-(3'→5'O,O-phosphorothioyl)-2'-O-methoxyethyl-5-methyluridylyl-(3'→5' O,O-phosphorothioyl)-2'-O-methoxyethyl-5-methyluridylyl-(3'→5' O,O-phosphorothioyl)-2'-O-methoxyethyl-5-methylcytosine, (3'→5' O,O-phosphorothioyl)-2'-O-methoxyethyl-5-methyluridylyl-19 sodium salt.

The oligonucleotide may be synthesized by a multi-step process that may be divided into two distinct operations: solid-phase synthesis and downstream processing. In the first operation, the nucleotide sequence of the oligonucleotide is assembled through a computer-controlled solid-phase synthesizer. Subsequent downstream processing includes deprotection steps, preparative reversed-phase chromatographic purification, isolation and drying to yield the oligonucleotide drug substance. The chemical synthesis of the oligonucelotide utilizes phosphoramidite coupling chemistry followed by oxidative sulfurization and involves sequential coupling of activated monomers to an elongating oligomer, the 3'-terminus of which is covalently attached to the solid support.

Detritylation (Reaction a).

Each cycle of the solid-phase synthesis commences with removal of the acid-labile 5'-O-4, 4'-dimethoxytrityl (DMT) protecting group of the 5' terminal nucleoside of the support bound oligonucleotide. This is accomplished by treatment with an acid solution (for example dichloroacetic acid (DCA) in toluene). Following detritylation, excess reagent is removed from the support by washing with acetonitrile in preparation for the next reaction.

Coupling (Reaction b)

Chain elongation is achieved by reaction of the 5'-hydroxyl group of the support-bound oligonucleotide with a solution of the phosphoramidite corresponding to that particular base position (e.g., for base2: MOE-$^{Me}C$ amidite) in the presence of an activator (e.g., 1H-tetrazole). This results in the formation of a phosphite triester linkage between the incoming nucleotide synthon and the support-bound oligonucleotide chain. After the coupling reaction, excess reagent is removed from the support by washing with acetonitrile in preparation for the next reaction.

Sulfurization (Reaction c)

The newly formed phosphite triester linkage is converted to the corresponding [O, O, O)-trialkyl phosphorothioate triester by treatment with a solution of a sulfur transfer reagent (e.g., phenylacetyl disulfide). Following sulfurization, excess reagent is removed from the support by washing with acetonitrile in preparation for the next reaction.

Capping (Reaction d)

A small proportion of the 5'-hydroxy groups available in any given cycle fail to extend. Coupling of these groups in any of the subsequent cycles would result in formation of process-related impurities ("DMT-on (n-l)-mers") which are difficult to separate from the desired product. To prevent formation of these impurities and to facilitate purification, a "capping reagent" (e.g., acetic anhydride and N-methylimidazole/acetonitrile/pyridine) is introduced into the reactor vessel to give capped sequences. The resulting failure sequences ("DMT-off shortmers") are separated from the desired product by reversed phase HPLC purification. After the capping reaction, excess reagent is removed from the support by washing with acetonitrile in preparation of the next reaction.

Reiteration of this basic four-step cycle using the appropriate protected nucleoside phosphoramidite allows assembly of the entire protected oligonucleotide sequence.

Backbone Deprotection (Reaction e)

Following completion of the assembly portion of the process the cyanoethyl groups protecting the (O, O, O)-trialkyl phosphorothioate triester internucleotide linkages are removed by treatment with a solution of triethylamine (TEA) in acetonitrile. The reagent and acrylonitrile generated during this step are removed by washing the column with acetonitrile.

Cleavage from Support and Base Deprotection (Reaction f)

Deprotection of the exocyclic amino groups and cleavage of the crude product from the support is achieved by incubation with aqueous ammonium hydroxide (reaction f). Purification of the crude, 5'-O-DMT-protected product is accomplished by reversed phase HPLC. The reversed phase HPLC step removes DMT-off failure sequences. The elution profile is monitored by UV absorption spectroscopy. Fractions containing DMT-on oligonucleotide product are collected and analyzed.

Acidic Deprotection (Reaction g)

Reversed phase HPLC fractions containing 5'-O-DMT-protected oligonucleotide are pooled and transferred to a precipitation tank. The products obtained from the purification of several syntheses are combined at this stage of the process. Purified DMT-on oligonucleotide is treated with acid (e.g., acetic acid) to remove the DMT group attached to the 5' terminus. After acid exposure for the prescribed time and neutralization, the oligonucleotide drug substance is isolated and dried.

Following the final acidic deprotection step, the solution is neutralized by addition of aqueous sodium hydroxide and the oligonucleotide drug substance is precipitated from solution by adding ethanol. The precipitated material is allowed to settle at the bottom of the reaction vessel and the ethanolic supernatant decanted. The precipitated material is redissolved in purified water and the solution pH adjusted to between pH 7.2 and 7.3. The precipitation step is repeated. The precipitated material is dissolved in water and the solution filtered through a 0.45 micron filter and transferred into disposable polypropylene trays that are then loaded into a lyophilizer. The solution is cooled to −50° C. Primary drying is carried out at 25° C. for 37 hours. The temperature is increased to 300° C. and a secondary drying step performed for 5.5 hours. Following completion of the lyophilization process, the drug: substance is transferred to high density polyethylene bottles and stored at −200° C.

Target Nucleic Acid

"Targeting" an antisense compound to a particular nucleic acid can be a multistep process. The process usually begins with the identification of a target nucleic acid whose function is to be modulated. In the present disclosure, the target nucleic acid encodes the α4 integrin chain of VLA-4 or α4β7 integrin.

The targeting process usually also includes determination of at least one target region, segment, or site within the target nucleic acid for the antisense interaction to occur such that the desired effect, for example, inhibition of expression, will result. The term "region" as used herein is defined as a portion of the target nucleic acid having at least one identifiable structure, function, or characteristic. Within regions of the target nucleic acids are segments. "Segments" are defined as smaller or sub-portions of regions within a target nucleic acid. "Sites" as used herein, means positions within the target nucleic acid.

Since the "translation initiation codon" is typically 5'-AUG (in transcribed mRNA molecules; 5'-ATG in the corresponding DNA molecule), the translation initiation codon is also referred to as the "AUG codon", the "start codon" or the "AUG start codon". A minority of genes have a translation initiation codon having the RNA sequence 5'-GUG, 5'-UUG, or 5'-CUG, and 5'-AUA, 5'-ACG and 5'-CUG have been shown to function in vivo. Thus, the terms "translation initiation codon" and "start codon" can encompass many codon sequences even though the initiator amino acid in each instance is typically methionine (in eukaryotes) or formylmethionine (in prokaryotes). It is also known in the art that eukaryotic and prokaryotic genes may have two or more alternative start codons, any one of which may be preferentially utilized for translation initiation in a particular cell type or tissue, or under a particular set of conditions. The terms "start codon" and "translation initiation codon" as used herein refer to the codon or codons that are used in vivo to initiate translation of an mRNA transcribed from a gene encoding, for example, α4 integrin chain of VLA-4 or α4β7 integrin, regardless of the sequence(s) of such codons.

A "translation termination codon" also referred to a "stop codon" may have one of three RNA sequences: 5'-UAA, 5'-UAG and 5'-UGA (5'-TAA, 5'-TAG and 5'-TGA, respectively in the corresponding DNA molecule). The terms "translation termination codon" and "stop codon" as used herein refer to the codon or codons that are used in vivo to terminate translation of an mRNA transcribed from a gene encoding the α4 integrin chain of VLA-4 or α4137 integrin, regardless of the sequence(s) of such codons.

The terms "start codon region" and "translation initiation codon region" refer to a portion of the mRNA or gene that encompasses from about 25 to about 50 contiguous nucleotides in either direction (i.e., 5' or 3') from the translation initiation codon. Similarly, the terms and "stop codon region" and "translation termination codon region" refer to a portion of the mRNA or gene that encompasses from about 25 to about 50 contiguous nucleotides in either direction (i.e., 5' or 3') from the translation termination codon. Consequently, the "start codon region" or "translation initiation codon region" and the "stop codon region" or "translation termination codon region" are all regions which may be targeted effectively with the antisense compounds of the present disclosure.

The "open reading frame" (ORF) or "coding region", which is known in the art to refer to the region between the translation initiation codon and the translation termination codon, is also a region which may be targeted effectively. In one embodiment, the intragenic region encompassing the translation initiation or termination codon of the ORF of a gene is targeted.

Other target regions include the 5' untranslated region (5'UTR), known in the art to refer to the portion of the mRNA in the 5' direction from the translation initiation codon, and thus including nucleotides between the 5' cap site and the translation initiation codon of the mRNA (or corresponding nucleotides on the gene), and the 3' untranslated region (3'UTR), known in the art to refer to the portion of the mRNA in the 3' direction from the translation termination codon, and thus including nucleotides between the translation termination codon and 3' end of the mRNA (or corresponding nucleotides on the gene). The 5' cap site of an mRNA comprises an N7-methylated guanosine residue joined to the 5'-most residue of the mRNA via a 5'-5' triphosphate linkage. The 5' cap region of an mRNA is considered to include the 5' cap structure itself, as well as the first 50 nucleotides adjacent to the cap site. In one embodiment, the 5' cap region is targeted.

Although some eukaryotic mRNA transcripts are directly translated, many contain one or more regions, known as "introns," which are excised from a transcript before it is translated. The remaining (and therefore translated) regions are known as "exons" and are spliced together to form a continuous mRNA sequence. mRNA transcripts produced via the process of splicing of two (or more) mRNAs from different gene sources are known as "fusion transcripts". In one embodiment, introns, or splice sites, that is, intron-exon junctions or exon-intron junctions, or aberrant fusion junctions due to rearrangements or deletions are targeted.

Alternative RNA transcripts can be produced from the same genomic region of DNA. These alternative transcripts are generally known as "variants".

"Pre-mRNA variants" are transcripts produced from the same genomic DNA that differ from other transcripts produced from the same genomic DNA in either their start or stop position and contain both intronic and exonic sequence. Upon excision of one or more exon or intron regions, or portions thereof during splicing, pre-mRNA variants produce smaller "mRNA variants". Consequently, mRNA variants are processed pre-mRNA variants and each unique pre-mRNA variant must always produce a unique mRNA variant as a result of splicing. These mRNA variants are also known as "alternative splice variants". If no splicing of the pre-mRNA variant occurs then the pre-mRNA variant is identical to the mRNA variant.

Variants can be produced through the use of alternative signals to start or stop transcription, that is through use of an alternative start codon or stop codon. Variants that originate from a pre-mRNA or mRNA that use alternative start codons are known as "alternative start variants" of that pre-mRNA or mRNA. Those transcripts that use an alternative stop codon are known as "alternative stop variants" of that pre-mRNA or mRNA. One specific type of alternative stop variant is the "polyA variant" in which the multiple transcripts produced result from the alternative selection of one of the "polyA stop signals" by the transcription machinery, thereby producing transcripts that terminate at unique polyA sites. In one embodiment, the pre-mRNA or mRNA variants are targeted.

The location on the target nucleic acid to which the antisense compound hybridizes is referred to as the "target segment". As used herein the term "target segment" is defined as at least an 8-nucleobase portion of a target region to which an antisense compound is targeted. While not wishing to be bound by theory, it is presently believed that these target segments represent portions of the target nucleic acid which are accessible for hybridization.

Once one or more target regions, segments or sites have been identified, antisense compounds are chosen which are sufficiently complementary to a target segment, that is, antisense compounds that hybridize sufficiently well and with sufficient specificity, to give the desired effect.

In a further embodiment, the target segment identified herein may be employed in a screen for additional compounds that modulate the expression of the α4 integrin gene (and thus expression of α4 integrin, VLA-4 and/or α4β7 integrin). "Modulators" are those compounds that decrease or increase the expression of a nucleic acid molecule encoding the α4 integrin chain of VLA-4 or α4β7 integrin and which comprise at least a 8 nucleobase portion which is complementary to a preferred target segment.

The screening method comprises the steps of contacting a target segment of the nucleic acid encoding the α4 integrin chain of VLA-4 or α4β7 integrin with one or more candidate modulators, and selecting for one or more candidate modulators which decrease or increase the expression of a nucleic acid encoding the α4 integrin chain of VLA-4 or α4β7 integrin. Once it is shown that the candidate modulator or modulators are capable of modulating (e.g., either decreasing or increasing) the expression of a nucleic acid encoding the α4 integrin chain of VLA-4 or α4β7 integrin, the modulator may then be employed in further investigative studies of the function of VLA-4 or α4β7 integrin, or for use as a research, diagnostic, or therapeutic agent.

The target segment may also be combined with its respective complementary antisense compound to form stabilized double-stranded (duplexed) oligonucleotides.

Such double stranded oligonucleotide moieties have been shown in the art to modulate target expression and regulate translation, as well as RNA processing via an antisense mechanism. Moreover, the double-stranded moieties may be subject to chemical modifications (Fire et al., 1998; Timmons and Fire, 1998; Timmons et al., 2001; Tabara et al., 1998; Montgomery et al., 1998; Tuschl et al., 1999; Elbashir et al., 2001a; Elbashir et al., 2001b). For example, such double-stranded moieties have been shown to inhibit the target by the classical hybridization of antisense strand of the duplex to the target, thereby triggering enzymatic degradation of the target (Tijsterman et al., 2002).

Compositions

Antisense compounds of the disclosure may be admixed, encapsulated, conjugated or otherwise associated with other molecules, molecule structures or mixtures of compounds, resulting in, for example, liposomes, receptor-targeted molecules, oral, rectal, topical or other formulations, for assisting in uptake, distribution and/or absorption.

Representative United States patents that teach the preparation of such uptake, distribution and/or absorption-assisting formulations include, but are not limited to, U.S. Pat. No. 5,108,921, U.S. Pat. No. 5,354,844, U.S. Pat. No. 5,416,016, U.S. Pat. No. 5,459,127, U.S. Pat. No. 5,521,291, U.S. Pat. No. 5,543,158, U.S. Pat. No. 5,547,932, U.S. Pat. No. 5,583,020, U.S. Pat. No. 5,591,721, U.S. Pat. No. 4,426,330, U.S. Pat. No. 4,534,899, U.S. Pat. No. 5,013,556, U.S. Pat. No. 5,108,921, U.S. Pat. No. 5,213,804, U.S. Pat. No. 5,227,170, U.S. Pat. No. 5,264,221, U.S. Pat. No. 5,356,633, U.S. Pat. No. 5,395,619, U.S. Pat. No. 5,416,016, U.S. Pat. No. 5,417,978, U.S. Pat. No. 5,462,854, U.S. Pat. No. 5,469,854, U.S. Pat. No. 5,512,295, U.S. Pat. No. 5,527,528, U.S. Pat. No. 5,534,259, U.S. Pat. No. 5,543,152, U.S. Pat. No. 5,556,948, U.S. Pat. No. 5,580,575, and U.S. Pat. No. 5,595,756.

Antisense compounds of the disclosure may be administered in a pharmaceutically acceptable carrier. The term "pharmaceutically acceptable carrier" refers to molecular entities that do not produce an allergic, toxic or otherwise adverse reaction when administered to a subject, particularly a mammal, and more particularly a human. The pharmaceutically acceptable carrier may be solid or liquid. Useful examples of pharmaceutically acceptable carriers include, but are not limited to, diluents, solvents, surfactants, excipients, suspending agents, buffering agents, lubricating agents, adjuvants, vehicles, emulsifiers, absorbants, dispersion media, coatings, stabilizers, protective colloids, adhesives, thickeners, thixotropic agents, penetration agents, sequestering agents, isotonic and absorption delaying agents that do not affect the activity of the active agents of the disclosure.

Antisense compounds of the disclosure may be pharmaceutically acceptable salts, esters, or salts of the esters, or any other compounds which, upon administration are capable of providing (directly or indirectly) the biologically active metabolite.

The term "pharmaceutically acceptable salts" as used herein refers to physiologically and pharmaceutically acceptable salts of the antisense compounds that retain the desired biological activities of the parent compounds and do not impart undesired toxicological effects upon administration. Preferred examples of pharmaceutically acceptable salts and their uses are further described in U.S. Pat. No. 6,287,860.

Antisense compounds of the disclosure may be prodrugs or pharmaceutically acceptable salts of the prodrugs, or other bioequivalents.

The term "prodrugs" as used herein refers to therapeutic agents that are prepared in an inactive form that is converted to an active form (i.e., drug) upon administration by the action of endogenous enzymes or other chemicals and/or conditions. In particular, prodrug forms of the antisense compounds of the disclosure are prepared as SATE [(S-acetyl-2-thioethyl) phosphate] derivatives according to the methods disclosed in WO 93/24510, WO 94/26764 and U.S. Pat. No. 5,770,713.

Administration

The antisense compounds of the disclosure are administered systemically. As used herein "systemic administration" is a route of administration that is either enteral or parenteral.

As used herein "enteral" refers to any form of administration that involves any part of the gastrointestinal tract and includes oral administration of, for example, the antisense oligonucleotide in tablet, capsule or drop form; gastric feeding tube, duodenal feeding tube, or gastrostomy; and rectal administration of, for example, the antisense compound in suppository or enema form.

As used herein "parenteral" includes administration by injection or infusion. Examples include, intravenous (into a vein), intraarterial (into an artery), intramuscular (into a muscle), intracardiac (into the heart), subcutaneous (under the skin), intraosseous infusion (into the bone marrow), intradermal, (into the skin itself), intrathecal (into the spinal canal), intraperitoneal (infusion or injection into the peritoneum), intravesical (infusion into the urinary bladder). transdermal (diffusion through the intact skin), transmucosal (diffusion through a mucous membrane), inhalational.

The antisense compound may be administered as single dose or as repeated doses on a period basis, for example, daily, once every two days, three, four, five, six seven, eight, nine, ten, eleven, twelve, thirteen or fourteen days, once weekly, twice weekly, three times weekly, or every two weeks.

The amount and frequency of administration may be determined by an attending physician. By way of example, a dose of 50-3400, more preferably 50-1600 mg antisense compound may be administered to a subject. A dose of 150-300 mg, for example, a dose of 200 mg is particularly contemplated for humans. A dose of 2, 3, 4, 5, 6, 7, 8, 9, or 10 mg/Kg is also particularly contemplated. A dose of greater than 5 mg/Kg is preferably administered at least 3 times weekly. A frequency of one single subcutaneous injection is preferred for doses up to 5 mg/Kg. For subcutaneous injections of doses greater than 5 mg/Kg, it is preferred the drug is administered as two simultaneous injections. In one embodiment, G-CSF and optionally Mozobil™ is added simultaneously.

In one embodiment, the antisense compound is administered at a dose of 4 mg/Kg per day, over 4, 5, 6, or 7 days for a total of 4, 5, 6, or 7 doses or the maximum tolerated dose.

In an alternate embodiment, the antisense compound is administered at dose of 4 or 6 mg/kg per day, every other day on day 1, 3, 5, for a total of 3 doses or the maximum tolerated dose.

The term "effective amount" as used herein refers to any dose of the antisense compound sufficient to effect stem and/or progenitor cell mobilization, under the conditions of administration.

In one embodiment, the average platelet count of a human subject is above 50,000 platelets/µL of blood during the course of administration. Not wishing to be limited by theory, it is possible that mobilization of $CD34^+$ progenitor cells enables rapid recovery of platelets and reduces the number of blood cell transfusions required following harvest.

In another embodiment, the administration is effective to provide a $C_{max}$ of the oligonucleotide in the plasma of the human subject upwards of 2890 ng/mL and preferably, of 10,000-11,000 ng/mL.

In another embodiment, the administration is effective to provide a $C_{min}$ or $C_{trough}$ of the oligonucleotide in the plasma of the human subject of at least 2.5 ng/mL, more preferably at least 20 ng/mL, and even more preferably at least 45 ng/mL.

The term "$C_{max}$" as used herein refers to the maximum or peak concentration of a drug observed after its administration. The term "$C_{min}$" as used herein refers to the minimum or trough concentration (i.e., $C_{trough}$ of a drug observed after is administration and just prior to the administration of a subsequent dose).

Combination Therapy

Antisense compounds of the invention may be administered in combination with one or more other mobilizing compounds/treatments.

Exemplary mobilizing treatments include administration of: low dose chemotherapy with for example, cyclophosphamide or melphalan; filgrastrim (G-CSF analogue, agonist; Neupogen™ (Amgen); Granulokine™ (HLR in Eastern Europe)); pegfilgrastim (G-CSF analogue, agonist; Neulastra™); lenograstim (G-CSF analogue, agonist; Granocyte™ (Chugai, Ligand Pharmaceuticals); sargramostim (GM-CSF analogue, agonist; Leukine™ (Bayer-Berlex)); plerixafor (CXCR4 antagonist, partial agonist to SDF-1; Mozobil™ (Genzyme)); ancestim (Stem cell factor (SCF); Stemgen™ (Amgen)).

Combination Therapy with One or More Growth Factors

In one embodiment, the methods of the present disclosure exploit the use of a growth factor in combination with an antisense compound to α4 integrin in the mobilization of stem and/or progenitor cells. The growth factor can be, for example, G-CSF, EPO, M-GDF, SCF, GM-CSF, M-CSF, CSF-1, SDF-1, IL-1, IL-2, IL-3, IL-4, IL-5, IL-6, IL-7, IL-8, IL-9, IL-10, IL-11, IL-12, or other various interleukins, IGF-1, LIF, interferon (such as a, β, gamma or consensus), neurotrophic factors (such as BDNF, NT-3, CTNF or noggin), other multi-potent growth factors (such as, to the extent these are demonstrated to be such multi-potent growth factors, flt-3/flk-2 ligand, stem cell proliferation factor, and totipotent stem cell factor), fibroblast growth factors (such as FGF), human growth hormone and analogs, fusion molecules, and other derivatives of the above.

The combination therapy compositions would be administered to a subject in a combined amount effective to mobilize stem and/or progenitor cells. This process may involve contacting the cells with the growth factor and the antisense compound to α4 integrin at the same time. This may be achieved by administering a single composition or pharmacological formulation that includes both agents, or by administering two distinct compositions or formulations, at the same time, wherein one composition includes the growth factor and the other includes the antisense compound to α4 integrin.

The growth factor treatment may precede or follow the treatment with the antisense compound to α4 integrin by an interval ranging from minutes to 1 or 2 weeks. The administration of the antisense compound to α4 integrin may precede the growth factor from minutes to several weeks. In embodiments where the antisense compound to α4 integrin and the growth factor are administered separately, one would generally ensure that a significant period of time did not expire between the times of each delivery, such that the antisense compound to α4 integrin and the growth factor would still be able to exert an advantageously combined effect. In such instances, it is contemplated that one would administer both the growth factor and antisense compound within about a few minutes, 4-6 hours, 6-12 hours, 12-24 hours or, within about 3 to 4 days of each other, with a delay time of only about 4-6 hours being most preferred, with the antisense compound drug administered second. In some situations, it may be desirable to extend the time period for treatment significantly, however, where several days (2, 3, 4, 5, 6, or 7) to several weeks (1, 2, 3, 4, 5, 6, 7, or 8) lapse between the respective administrations, for example, in instances where the antisense compound is administered first.

G-CSF

In one embodiment, the methods of the present disclosure exploit the use of G-CSF in combination with an antisense compound to α4 integrin in the mobilization of stem and/or progenitor cells. In one embodiment, the use of G-CSF in combination with an antisense compound to α4 integrin results in the mobilization of CD34$^+$ multipotent and/or oligopotent cells.

G-CSF causes an increase in the release of hematopoietic stem cells into the blood, and plays a role in the proliferation, differentiation, and survival of myeloid progenitor cells (Takano et al., 2003). G-CSF and other hematopoietic growth factors including IL-3, IL-6, GM-CSF, and SCF have all been reported to be positive regulators of granulopoiesis (the production of granulocytes) in the bone marrow (Takano et al., 2003). The present inventors have shown that administration of an antisense compound to α4 integrin in combination with G-CSF increases the release of CFU-GEMM and CD34$^+$ cells. Isolation and transplant of these cells may be used to treat, for example, a patient in need of granulocytes.

G-CSF also has been shown to specifically stimulate the proliferation and differentiation of neutrophilic precursor cells into mature neutrophils (Fukunaga et al., 1993), and is well known for its usefulness in the treatment of neutropenic states (Welte, 1985; Souza et al., 1986; Gabrilove, 1989). G-CSF increases the number of circulating granulocytes and has been reported to ameliorate infection in sepsis models. G-CSF administration also inhibits the release of tumor necrosis factor (TNF), a cytokine important to tissue injury during sepsis and rejection (Wendel et al., 1992).

Accordingly, G-CSF has been found to be useful in the treatment of conditions where an increase in neutrophils will provide benefits. For example, for cancer patients, G-CSF is beneficial as a means of selectively stimulating neutrophil production to compensate for hematopoietic deficits resulting from chemotherapy or radiation therapy. Other indications include treatment of various infectious diseases and related conditions, such as sepsis, which is typically caused by a metabolite of bacteria. G-CSF is also useful alone, or in combination with other compounds, such as other cytokines, for growth or expansion of cells in culture (for example, for bone marrow transplants or ex vivo expansion). G-CSF has been administered to transplant patients as an adjunct to treatment of infection or for treatment of neutropenia (Diflo et al., 1992; Wright et al., 1991; Lachaux et al., 1993; Colquehoun et al., 1993).

In one embodiment, administration of the antisense compound to α4 integrin does not result in neutrophilia and may even result in neutropenia. Combination of the antisense compound with G-CSF provides an unexpected advantage over combination of G-CSF with, for example, Mozobil™ which may result in additional neutrophilia beyond G-CSF that requires monitoring.

G-CSF is produced by fibroblasts, macrophages, T cells, trophoblasts, endothelial cells, and epithelial cells, and is the expression product of a single copy gene comprised of four exons and five introns located on chromosome seventeen. In humans, endogenous G-CSF is detectable in blood plasma (Jones et al., 1989). G-CSF is species cross-reactive, such that when human G-CSF is administered to another mammal, such as a mouse, canine, or monkey, sustained neutrophil leukocytosis is elicited (Moore et al., 1987).

G-CSF can be obtained and purified from a number of sources. G-CSF can be isolated from the supernatants of cultured tumor cell lines. The development of recombinant DNA technology has enabled the production of commercial scale quantities of G-CSF in glycosylated form as a product of eukaryotic host cell expression, and of G-CSF in non-glycosylated form as a product of prokaryotic host cell expression.

G-CSF compositions or formulations may be selected based on the route of administration and may include liposome and micelle formulations as well as classic pharmaceutical preparations.

In a preferred embodiment, G-CSF protein-based therapy is effected via continuous or intermittent intravenous administration. By "effective amount" it is meant an amount of G-CSF polypeptide that is sufficient to support an observable change in the level of one or more biological activities of G-CSF. The change may be an increased level of G-CSF activity. Preferably, the change is an increase in bone marrow stem cell mobilization.

It is contemplated that the specific activity of a G-CSF protein preparation may be in the range of about 100 units/mg of protein to about 500 units/mg protein. Thus, a given preparation of a human G-CSF protein may comprise about 100 units/mg protein, about 125 units/mg protein, about 150 units/mg protein, about 175 units/mg protein, about 200 units/mg protein, about 225 units/mg protein, about 250 units/mg protein, about 275 units/mg protein, about 300 units/mg protein, about 325 units/mg protein, about 350 units/mg protein, about 375 units/mg protein, about 400 units/mg protein, about 425 units/mg protein, about 450 units/mg protein, about 475 units/mg protein and about 500 units/mg protein. A particularly preferred range is from about 100 units/mg protein to about 200 units/mg protein. A more preferable range is between about 150 to about 200 units/mg protein. Preferably, the protein composition is substantially free of contaminating factors, having a contamination level of less than 0.02% (w/w). G-CSF compositions, suitable for injection into a patient, can be prepared, for example, by reconstitution with a pharmacologically acceptable diluent of a lyophilized sample comprising purified G-CSF and stabilizing salts.

Administration of the compositions can be systemic or local, and may comprise a single site injection of an effective amount of the G-CSF protein composition. Any route known to those of skill in the art for the administration of G-CSF is contemplated including, for example, intravenous, intramuscular, subcutaneous or a catheter for long-term administration. Alternatively, it is contemplated that the G-CSF may be delivered to the subject at multiple sites. The multiple administrations may be rendered simultaneously or may be administered over a period of several hours. In certain cases, it may be beneficial to provide a continuous flow of the composition. Additional therapy may be administered on a period basis, for example, daily, weekly, or monthly.

In one embodiment, G-CSF is administered for a period of 4, 5, 6, or 7 days, or as recommended by the manufacturer. Neupogen™ is typically injected subcutaneously 10 μg/kg/day daily over 4 days before the first apheresis procedure on day 5, and optionally, on day 5, 6 and 7 if not enough stem and/or progenitor cells are released.

Derivatives of G-CSF are also comprehended herein. Such derivatives include molecules modified by one or more water soluble polymer molecules, such as polyethylene glycol, or by the addition of polyamino acids, including fusion proteins (procedures for which are well-known in the art). Such derivatization may occur singularly at the N- or C-terminus or there may be multiple sites of derivatization. Substitution of one or more amino acids with lysine may provide additional sites for derivatization. (U.S. Pat. No. 5,824,784 and U.S. Pat. No. 5,824,778).

Harvesting Stem and Progenitor Cells from Peripheral Blood

In one embodiment, the stem and/or progenitor cells are mobilized into the peripheral blood. The stem and/or progenitor cells can be isolated from the peripheral blood of the subject. Peripheral blood can be collected without the use of general anesthesia, and the procedure is usually performed on an outpatient basis with little or no discomfort during, or after, the collection.

The stem and/or progenitor cells are preferably isolated from the peripheral blood of the subject through a process known as apheresis. The stem and/or progenitor cells may be further purified by using fluorescence activated cell sorting or density gradient centrifugation. For example, cells expressing CD34 may be purified from the apheretic sample by fluorescence activated cell sorting. The stem and/or progenitor cells may be expanded and/or differentiated ex vivo, stored for future use, or injected into a patient. The patient may be the subject whose blood had been collected or a HLA-matched subject.

In one embodiment, the first apheresis is conducted on day 5, and follow up apheresis on days 6 and 7, and if not enough stem cell/progenitor cells are collected, apheresis may conducted daily to day 14.

Typically more than $2 \times 10^6$ CD34$^+$ cells/Kg are sought to be isolated and used in a human graft. In one example, $5 \times 10^6$ CD34$^+$ cells/Kg are isolated for transplant in non-Hodgkin's lymphoma, and $6 \times 10^6$ CD34$^+$ cells/Kg are isolated for transplant in Multiple Myeloma. Preferably $5 \times 10^6$ CD34$^+$ cells/Kg are isolated in up to 4 apheresis for transplant in non-Hodgkin's lymphoma, and $6 \times 10^6$ CD34$^+$ cells/Kg are isolated in up to 2 apheresis in multiple myeloma. Typically, mobilization with G-CSF alone or G-CSF with other mobilizing agents, like Mozobil™, is used to release CD34$^+$ cells to the periphery. The G-CSF Neupogen™ is effective in about 30 and 40% of multiple myeloma and non-Hodgkin's lymphoma patients respectively, in achieving this number of cells/Kg. Mozobil™ in combination with Neupogen™ is effective in another 40% and 30% of multiple myeloma and non-Hodgkin's lymphoma patients respectively. Thus, about two-thirds and one third of treatments are suboptimal with existing monotherapy and combination treatments, respectively. The antisense compounds of the present disclosure, target a novel mechanism compared to Neupogen™ and Mozobil™ to improve release and reduce the number of apheresis.

Existing treatments may also release contaminant effector T cells causing graft versus host disease in allogeneic transplants or too many neutrophils or contaminant tumor cells in the case of autologous transplants. The antisense compounds of the present disclosure are to a different target, and are more selectively taken up by cells as shown in Example 4 and 5, and do not release neutrophils, providing potential safety improvements over existing treatments.

Uses of Stem and Progenitor Cells Harvested According to Methods of the Disclosure.

Stem and/or progenitor cells harvested according to methods of the disclosure can be used in the treatment of diseases and conditions which require stem and/or progenitor (or effector) cell transplants. For example, the stem and/or progenitor cells can be used for the treatment of failure or dysfunction of normal blood cell production and maturation, hematopoietic malignancy, autoimmune disease, liver disease, or immunodeficiency (by reason of for example, irradiation, chemotherapy or infection with a pathogen).

The transplant typically includes some cells that are true, long-term self-renewing stem cells, some shorter-term progenitors, and some non-stem cells.

The stem and/or progenitor cells may be expanded or differentiated ex vivo prior to administration to a patient. For example, the stem and/or progenitor cells may be differentiated into effector hepatocyte cells and transplanted into patients suffering from liver disease.

As used herein, the term "treatment" includes abrogating, inhibiting, slowing, or reversing the progression of a disease or condition, or ameliorating or preventing a clinical symptom of the disease or condition.

Leukemia and Lymphoma

Stem and progenitor cells harvested according to methods of the disclosure can be used in the treatment of cancers of the blood—leukemia and lymphoma, which result from the uncontrolled proliferation of white blood cells and progenitors. In one embodiment, the patient's own cancerous hematopoietic cells are destroyed via radiation or chemotherapy, then replaced with a transplant of stem and progenitor cells harvested from the peripheral blood of a matched (allogeneic) donor. In another embodiment the patient's own hematopoietic stem and progenitor cells are collected prior to the radiation or chemotherapy, and subsequently returned. Cancers of the blood include acute lymphoblastic leukemia, acute myeloblastic leukemia, chronic myelogenous leukemia (CML), Hodgkin's disease, multiple myeloma, and non-Hodgkin's lymphoma.

Inherited Blood Disorders

Another use of allogeneic stem and progenitor cells harvested according to methods of the disclosure is in the treatment of hereditary blood disorders, such as different types of inherited anemia (failure to produce blood cells), and inborn errors of metabolism (genetic disorders characterized by defects in key enzymes needed to produce essential body components or degrade chemical byproducts). The blood disorders include aplastic anemia, beta-thalassemia, Blackfan-Diamond syndrome, globoid cell leukodystrophy, sickle-cell anemia, severe combined immunodeficiency, X-linked lymphoproliferative syndrome, and Wiskott-Aldrich syndrome. Inborn errors of metabolism that may be treated with bone marrow transplants include: Hunter's syndrome, Hurler's syndrome, Lesch Nyhan syndrome, and osteopetrosis.

Hematopoietic Stem Cell Rescue in Cancer Chemotherapy

Chemotherapy, aimed at rapidly dividing cancer cells inevitably targets rapidly dividing hematopoietic, cells. Autologous stem and progenitor cells harvested according to methods of the disclosure can be used to replace the cells destroyed by chemotherapy. Because patients are transplanted with their own cells, there is no chance of immune mismatch or graft-versus-host disease.

Graft-Versus-Tumor Treatment of Cancer

Stem and progenitor cells harvested according to methods of the disclosure may be used to treat otherwise untreatable tumors, in particular, solid tumors that resist standard therapy, including cancer of the lung, prostate, ovary, breast, colon, esophagus, liver, and pancreas.

This treatment relies on an allogeneic stem or progenitor cell transplant. The subject's own immune system is suppressed, but not totally destroyed. The donor's cells are transfused into the patient, and the patient's immune cells closely monitored using, for example, DNA fingerprinting, to follow the engraftment of the donor's cells and regrowth of the patient's own blood cells. The patient's immune system may need to be further suppressed to deter their T cells from attacking the graft and to reduce graft-versus-host disease.

Other Applications

Stem and progenitor cells harvested according to methods of the disclosure may be used to treat autoimmune diseases, such as type 1 diabetes, rheumatoid arthritis, and system lupus erythematosis.

Stem and progenitor cells harvested according to methods of the disclosure may also be used as a means to deliver genes to repair damaged cells (i.e., for gene therapy).

EXAMPLES

Example 1: Mouse Pharmacology Mobilization Studies

This study evaluated myeloid progenitor mobilization using antisense to mouse VLA-4 in combination with G-CSF in an in vivo murine model.

Animals:

Thirty female C57BL/6 mice 6-8 weeks of age were purchased from Jackson Laboratory and housed and treated at the British Columbia Cancer Agency (BCCA, Vancouver, B.C., Canada).

Compound:

ISIS 348574 (ATATTTTTCCACCTGTGCCC: SEQ ID NO: 2), a 5-10-5 MOE gapmer with a phosphorothioate backbone and 5-methylcystosine for every C that is fully complementary to mouse and rat α4 integrin (mouse and rat CD49d) was used in these studies. ISIS348574 has a MW of 7138.23 Da and EXT Coeff of 180.0 mM. Analysis of this oligonucleotide targeting mouse VLA-4 is as described in WO 2006/086821.

TABLE 2

Summary of nucleic acid molecules

| ISIS No. | Sequence | SEQ ID NO. | % Inhibition | Species oligonucleotide targets |
|---|---|---|---|---|
| 348574 | ATATTTTTCCACCTGTGCCC | 2 | 60.3 | Mouse/Rat |

Animal Treatment Schedule

Six groups of mice (5 mice per group) were treated with saline control or test compounds Neulasta™, a clinical grade pegylated form of G-CSF, or ISIS 348574, an antisense compound to mouse VLA-4 (mVLA-4), in accordance with the schedule summarized in Table 3.

The mVLA-4 antisense compound (0.8 mL aliquots at 6 mg/mL) was injected based on mouse weight to obtain a final antisense dose of 30 mg/Kg. mVLA-4 antisense compound was injected for a period of 4, 7, 10 or 14 days for a total of 2, 3, 5 or 7 doses. Three days prior to harvest, all antisense treatment groups and the G-CSF only treatment group were injected with one 50 µg dose of Neulasta™. A control group received doses of saline vehicle for 14 days with no injection of G-CSF.

TABLE 3

Summary of treatment schedule

| Group | Treatment | Doses |
|---|---|---|
| 1 | Antisense (30 mg/Kg for a period of 14 days) + G-CSF (one 50 ug dose 3 days before sacrifice) | 7 ASO |
| 2 | Antisense (30 mg/Kg for a period of 10 days) + G-CSF (one 50 ug dose 3 days before sacrifice) | 5 ASO |
| 3 | Antisense (30 mg/Kg for a period of 7 days) + G-CSF (one 50 ug dose 3 days before sacrifice) | 3 ASO |
| 4 | Antisense (30 mg/Kg for a period of 4 days) + G-CSF (one 50 ug dose 3 days before sacrifice) | 2 ASO |
| 5 | G-CSF only (one 50 ug dose 3 days before sacrifice) | 0 ASO |
| 6 | Saline control (saline doses for 14 days) | 7 saline |

All mice were sacrificed in accordance with the Canadian Council on Animal Care Guidelines 14 days after the initiation of the study. Peripheral blood samples were collected in EDTA microtainer tubes by cardiac puncture and processed for colony forming cell (CFC) and flow cytometric analysis.

Cell Processing

The volume of each sample was recorded and nucleated cell counts performed using 3% acetic acid and a Neubauer counting chamber. From these, the total number of nucleated cells per mL of peripheral blood was calculated for each individual mouse. Red blood cells (RBC) were lysed with ammonium chloride buffer, nine times v/v of blood for 10 minutes on ice, and the samples washed once in Iscove's Modified Dulbecco's Medium (IMDM) plus 2% Fetal Bovine Serum (FBS). The cell pellet was then resuspended in a known volume of IMDM plus 2% FBS and nucleated cell counts evaluated to determine cell concentration. From this stock of cells, a dilution of $2\times10^6$ cells/mL was prepared to assess hematopoietic progenitor content and remaining cells were used for flow cytometric analysis.

Flow Cytometry

To assess expression of the murine Scal (Ly-6A/E) marker, cells were incubated with Sca-1 PE conjugated antibody (clone E13-161.7, BD Pharmingen, lot 29286, exp. 2011-05-31) and a series of FITC conjugated lineage markers (CD5, CD45R, Gr-1, CD11b, Ter119). The antibody cocktail was added to approximately $1\times10^6$ cells in 100 µL and incubated at 4° C. for 30 minutes. Cells were then briefly incubated with ACK lysis buffer to lyse any remaining red blood cells. Tubes containing cells and non-relevant FITC and PE labeled antibodies were set up to establish appropriate compensation of fluorochromes. Tubes for cytometer set up were washed with PBS plus 2% FBS and sample tubes were washed with PBS+2% FBS containing propidium iodide (PI) at 1 µg/mL to label dead cells. Flow cytometric analysis of only live cells was performed using CELLQuest software after collection of up to 100,000 events. In an effort to obtain further information on alternate progenitor markers, cells were stored overnight at 4° C. and the following day stained with EPCR PE (clone RMEPCR1560, STI), c-kit APC (clone 2B8, BD Pharmingen, lot 27108, exp. 2008-04-30) and FITC conjugated lineage markers following the previous procedure.

Clonogenic Assays

Clonogenic progenitors of the erythroid (BFU-E), granulocyte-monocyte (CFU-GM) and multipotential/oligopotential (CFU-GEMM) lineages were assessed in methylcellulose-based medium MethoCult™ M3434 containing 50 ng/mL rm Stem Cell Factor, 10 ng/mL rm Interleukin 3, 10 ng/mL rh Interleukin 6 and 3 U/mL rh Erythropoietin. Peripheral blood cells from each mouse were added to MethoCult™ M3434, vortexed and plated in triplicate at $2\times10^5$ cells/dish. Cultures were incubated for 10 days at 37° C., 5% $CO_2$ in humidified incubators.

Statistical Analysis

The mean+/−1 standard deviation was calculated for data sets in each group and for triplicate cultures of clonogenic assays for each mouse. Standard t-tests were performed to assess if there was a difference in the number of cells or colonies generated between control and treated cultures. Due to the potential subjectivity of colony enumeration, a p value of less than 0.01 is deemed significant.

Mouse Study Colony Forming Cells

Progenitor colony forming cell assays were used to determine the mobilization of myeloid progenitors from the bone marrow into the peripheral blood following the treatment of mice with various dosing regimens of mVLA-4 antisense compound and G-CSF.

The percentage of granulocyte, erythrocyte, monocyte, megakaryocyte multipotential/oligopotential progenitors (GEMM; $CD34^-$, $CD33^+$, $CD13^+$, $HLADR^+$) was 70% higher at day 7 and day 10 and 85% higher at day 14 following treatment with mVLA-4 antisense compound and G-CSF compared to treatment with G-CSF alone.

The percentage of granulocyte, macrophage progenitors (CFU-GM; $CD34^+$, $CD33^+$, $CD13^+$, $HLADR^+$) derived from GEMM, which have low proliferative potential, trends up approximately 18% by day 10 and day 14 following treatment with mVLA-4 antisense compound and G-CSF compared to treatment with G-CSF alone.

The percentage of earliest erythroid progenitors (BFU-E) derived from GEMM, which have low proliferative potential, was unchanged following treatment with mVLA-4 antisense compound and G-CSF compared to treatment with G-CSF alone.

Total colony forming colonies increased by approximately 20% as CFU-GM is the most prevalent colony forming unit.

Treatment with mVLA-4 antisense compound and G-CSF surprisingly mobilized 12 times more ($p<0.01$) myeloid precursor GEMM cells compared to G-CSF alone which mobilized 7 times more GEMM cells compared to saline control. Further, it was surprising that there was only a limited increase in CFU-GM cells and no detectable BFU-E cells in the peripheral blood following treatment with mVLA-4 antisense compound and G-CSF.

Treatment with G-CSF alone appears to have an effect on GEMM ($p=0.05$-$0.07$) and has an effect on CFU-GM (X12 fold) and BFU-E (2.5×).

mVLA-4 antisense compound appears to start to have GEMM releasing effects in 4 days and works within 7 to 10 days to release (in combination with G-CSF) 12 times more GEMM cells (multipotent/oligopotent progenitor cells), which can repopulate all granulocytes, erythrocytes, monocytes and megakaryocytes.

Mouse Study Flow Cytometry Analysis of Cells

Flow cytometry was used to determine the mobilization of progenitors and stem cells from the bone marrow into the peripheral blood following the treatment of mice with various dosing regimens of mVLA-4 antisense compound and G-CSF.

Treatment with mVLA4 antisense compound and G-CSF increased EPCR$^+$ cells 55% after 10 days following treatment with mVLA-4 antisense compound and G-CSF compared to treatment with G-CSF alone but not when compared to saline. The long acting G-CSF added in the last 3 days in these studies appears to have reduced the % EPCR+ cells versus saline.

EPCR is the endothelial protein C receptor, also known as CCD41 or CD201. EPCR protein is detected on ~1.5% of mouse bone marrow cells. Purified EPCR$^+$ cells are reported to be highly enriched for hematopoietic stem cell activity. The percentage of EPCR$^{++}$ cells is possibly the best marker of mouse hematopoietic stem cells in the study. High EPCR expressing cells are thought to be able to reconstitute bone marrow when transplanted. EPCR$^+$ cells in mice may be the equivalent of the earliest human hematopoietic stem cells.

Treatment with mVLA4 antisense compound and G-CSF caused leukopenia. G-CSF treatment alone would normally increase neutrophils, which are a major leukocyte population in mouse blood, so it is possible the mVLA-4 antisense compound caused the decrease in leukocytes. ATL1102 (hVLA-4) also reduces some blood cells in the human studies, which is not what occurs with antibodies to VLA-4 as described below in Example 8.

Example 2: Human Pharmacology CD34 Mobilization Studies

This study evaluated CD34 cell mobilization using antisense to humanVLA-4 in an in vivo human study. CD34 RNA levels were detected via PCR in total blood RNA.

Compound:

ISIS 107248 (CTGAGTCTGTTTTCCATTCT: SEQ ID NO: 1), a 3-9-8 MOE gapmer with a phosphorothioate backbone and 5-methylcystosine for every C that is fully complementary to human α4 integrin (CD49d) was used in these studies. Analysis of this oligonucleotide also known as ATL1102 (hVLA-4 antisense oligonucleotide) and others targeting human VLA-4 in vitro is as described in WO 2000/20635 and U.S. Pat. No. 6,258,790.

The subcutaneous solution for injection contained only ATL1102, in water for injection adjusted to pH 7.4 with acid or base during compounding. The solution was clear with a light yellow color. It was packaged in Type I, flint glass vial that was stoppered with a bromobutyl rubber closure having a Teflon® coating and sealed with an aluminum flip-off overseal.

Treatment of Multiple Sclerosis Patients:

ATL1102 was administered to multiple sclerosis patients in a double blind placebo controlled study and the effect of the drug on the number of brain lesions was determined by magnetic resonance imaging. The treatment details in relapse remitting multiple sclerosis patients (RRMS) and analysis of this oligonucleotide in terms of reduced lesion numbers is as described in WO 2010/008474.

CD34 Mobilization Studies in an In Vivo Human Model:

Total blood RNA prepared from several MS patients was evaluated for CD34+ (hematopoietic) stem cell and progenitor mobilization. CD34$^+$ cell mobilization was studied in 11 subjects diagnosed with RRMS who received ATL1102 (hVLA-4 antisense oligonucleotide) by subcutaneous injections for whom total blood RNA at week 8 of treatment and baseline was available.

RNA Isolation and cDNA Preparation was as Per Example 3 Below.

TaqMan Real-Time Quantitative PCR for CD34

Real-time quantitative RT-PCR for CD34 was done as previously described by Oppliger et al., Hematologica 2005 90(7):875-880.

CD34 RNA Transcript Analysis

ATL1102 treatment increased CD34 transcripts in total blood RNA 1.5 fold (P<0.027) at week 8 compared to baseline in the 11 matched RRMS patients compared to the PBGD housekeeping gene expressed in all cells in total blood, including red blood cells (Table 4).

TABLE 4

| Patient | Baseline | Week 8 | Change |
|---|---|---|---|
| AS21 | 0.028 | 0.027 | 0.964 |
| AS30 | 0.020 | 0.048 | 2.400 |
| AS33 | 0.013 | 0.037 | 2.789 |
| AS36 | 0.020 | 0.020 | 1.000 |
| AS40 | 0.011 | 0.008 | 0.685 |
| AS42 | 0.020 | 0.027 | 1.329 |
| AS46 | 0.025 | 0.029 | 1.145 |
| AS47 | 0.014 | 0.027 | 1.952 |
| AS52 | 0.021 | 0.028 | 1.333 |
| AS54 | 0.015 | 0.013 | 0.880 |
| AS49.73 | 0.028 | 0.049 | 1.753 |
| Mean | 0.020 | 0.029 | |
| SD | 0.006 | 0.013 | |
| Mean change | | | 1.476 |
| | | | P < 0.0273 |

Example 3: Human VLA-4 RNA Pharmacodynamic Studies

This study evaluated VLA RNA effects using hVLA-4 antisense in the above identified in vivo human multiple sclerosis study in example 2. CD49d RNA levels were detected via PCR in whole blood RNA or fractionated CD4$^+$ and CD8$^+$ lymphocyte RNA.

RNA Isolation

For samples from the east Europe centers, the Paxgene® Blood RNA System tubes (PreAnalytiX, Qiagen GmbH) were used. 2.5 ml of whole blood was drawn directly in Paxgene® tubes and treated as indicated in the manufacture's instructions. By this method, intracellular RNA was stabilized until needed. RNA isolation was preformed using the Paxgene® Kit according to the manufactures instructions.

For samples from the German centers RNA-isolation occurred as follows: 2-8 hours after withdrawal of 24 mL EDTA blood, a pre enrichment of lymphocytes was done using the Ficoll based separation solution LSM 1077 (PAA). Cells were counted and immediately used for magneto-immuno-isolation of CD4+ and CD8+ cells using a CD4 and CD8 positive isolation Kit (Dynal) according to the manufacturer's manual. Purity of CD4$^+$ and CD8$^+$ isolated cell was checked randomly by flow cytometry. RNA isolation was performed using the RNeasy Kit (Qiagen GmbH) according to the manufacture's instructions. In addition, 2.5 mL of the EDTA blood was directly drawn in a Paxgene® Blood RNA System tube (PreAnalytiX, Qiagen GmbH) and RNA isolation was preformed using the Paxgene® Kit according to the manufacture's instructions.

cDNA Preparation cDNA was produced as polymerase chain reaction (PCR) template using AffinityScript QPCR cDNA Synthesis Kit (Stratagene). The reaction mixture contained 6 L of total RNA, 3 L of random primers (0.1 µg/µl), 10 µL of first strand master mix (2×) and 1 µL of AffinityScript RT/RNase Block enzyme mixture. The reaction was incubated at 25° C. for 5 minutes, 42° C. for 15 minutes and at 95° C. for 5 minutes.

Real-Time PCR for Amplification of Human VLA-4

The PCR was performed on a 7500 Real-Time PCR System (AppliedBiosystems). For the amplification of hITGA4 (VLA-4), the reaction mixture included 5 ng of cDNA, 1.25 µL of TaqMan expression assay (20×, Hs00168433_ml, AppliedBiosystems) and 12.5 µL TaqMan Expression Master Mix (2×, AppliedBiosystems) in a total volume of 25 µL. For the amplification of the housekeeping gene hTBP (human TATA box binding protein), the reaction mixture included 5 ng of cDNA, 1.25 L of TaqMan expression assay (20×, Hs00427620_ml, AppliedBiosystems) and 12.5 µL TaqMan Expression Master Mix (2×, AppliedBiosystems) in a total volume of 25 µL.

The PCRs for hITGA4 and hTATA were conducted in separate wells as duplicates per run. For each sample, two runs were performed. Each reaction was performed as follows: an initial incubation at 50° C. for 2 minutes and enzyme activation at 95° C. for 10 minutes followed by 40 cycles of 95° C. for 15 seconds and 60° C. for 1 minute. The data collection took place at the 60° C. incubation step.

Relative Quantification of Human VLA-4

The expression level of hITGA4 mRNA in each sample was analyzed by SDS v1.2 software (AppliedBiosystems). The principles and workflows have been described previously (Applied Biosystems User Bulletin No. 2 (P/N 4303859); Livak and Schmittgen, 2001).

Relative quantification determines the change in expression of a nucleic acid sequence (target) in a test sample relative to the same sequence in a calibrator sample (a sample used as the basis for comparative results). The purpose of the endogenous control gene (housekeeping gene) is to normalize the PCR for the amount of RNA added to the reverse transcription reaction. The comparative $C_T$ Method ($\Delta\Delta C_T$ Method) uses arithmetic formulas to achieve the result for relative quantification. For this method it is not necessary to use standard curves as long as the PCR efficiencies between target and endogenous control are relatively equivalent.

The amount of target, normalized to an endogenous reference (Ct target gene−Ct Endogeneous control=$\Delta C_T$) and relative to a calibrator ($\Delta C_T$ sample−$\Delta C_T$ Calibrator=$\Delta\Delta C_T$), is given by: $2^{-\Delta\Delta C}T$; $C_T$=threshold cycle.

In this experiment, the RNA of a healthy untreated test person was used as the calibrator sample and it was verified that the efficiencies of the target—and the housekeeping gene-PCR were comparable ($\Delta$ Efficiency≤0.02). A $C_T$ threshold of 0.2000000 and a baseline from cycle 3 to 15 was chosen.

Results

There were no changes in CD49d RNA levels detected in whole blood or fractionated CD4$^+$ and CD8$^+$ lymphocytes on a per microgram basis. CD49d RNA analysis in whole blood may have been affected by the reduction in neutrophils, which cells occur in great numbers in human blood, and are mostly VLA-4 RNA negative. Absence of CD49d RNA reduction in CD4 and CD8 lymphocytes indicate ATL1102 reduces VLA-4 RNA on only a select number of blood T cells and absence of reduction in total blood may indicate ATL1102 reduces VLA-4 RNA in only a select number of other blood cells. This is consistent with the observations in examples 4 and 5.

Example 4: Human VLA-4 Cellular Pharmacodynamic Studies

Blood samples were obtained on visits 2 (baseline), 6 (week 8), 7 (week 12), and 8 (week 16) from the RRMS patients in example study 2 for evaluating VLA-4 levels on the cell surface. 36 ml whole blood was needed for VLA-4 assay on lymphocytes.

Cell Surface Antigenic Determinants

Multi-channel flow cytometry analysis of patient blood samples for cell surface expression of VLA-4 and markers of leucocyte sub-populations was performed. Studies were conducted on CD3$^+$ T cells, CD4$^+$ T cells, CD8$^+$ T cells, CD19$^+$ B cells and CD14$^{+o}$ monocytes and VLA-4 co-staining was analyzed as VLA-4 MFI or as the percentage of VLA-4$^+$ cells within a given cell population.

Measurement of VLA-4 Cell Surface Expression

Whole blood mononuclear cells were analyzed for VLA-4 membrane expression by flow cytometry using the monoclonal antibody (MoAb) fluorescein isothiocyanate (FITC)-conjugated anti-CD49d (VLA-4; Acris Antibodies, Hiddenhausen, Germany). In short, to 200 µL phosphate buffered saline (PBS), 10 µL of the VLA-4 MoAb was added. To identify B cells, 10 µL phycoerythrin (PE)-conjugated anti-CD19 MoAb was added. To identify monocytes, 2 µL allophycocyanin (APC)-conjugated anti-CD14 MoAb was added. To identify T cells and their CD4$^+$ and CD8$^+$ sub-populations, 10 µL perinidin chlorophyll protein (PerCP)-conjugated anti-CD3 MoAb, 10 µL PE-conjugated anti-CD4 MoAb, and 2 µL APC-conjugated anti-CD8 MoAb was added. After addition of 100 µL EDTA-blood, samples were incubated in the dark for 15 minutes. The erythrocytes were lysed with lysing solution (Becton Dickinson, Heidelberg, Germany) and then washed with PBS. Stained cells were measured with a FACSCalibur (Becton Dickinson) and VLA-4 expression was recorded as percentage of cells as well as mean channel fluorescence intensity (MFI). MoAB directed against B cells, T lymphocytes and monocytes were purchased from Becton Dickinson.

Statistical analysis of placebo and baseline comparisons have been performed for the flow cytometry data by two methods. The first method involved analysis of covariance tests of untransformed and log transformed data, with the log transformed data reported below to determine the % reduction, and where data was excluded when there is no corresponding baseline value. The second method involved using a Student T test of untransformed data where all data was included.

Results

B Cell Surface VLA-4 Effects

ATL1102 treatment resulted in a reduction in the percentage of CD19$^+$ B lymphocytes expressing detectable VLA-4. This was observed at week 8 compared to both placebo group and baseline.

In placebo comparisons, an 11% reduction ($p<0.05$) was observed by the first method of analysis. An 8.3% reduction ($p<0.013$) was observed by the second method analysis of the VLA-4+/CD19$^+$ B cell number data.

In baseline comparisons, a similar reduction in the percentage of VLA-4$^+$/CD19$^+$ B cells was observed. An 11% reduction ($p<0.05$) was observed by first method of analysis, and a 7.1% reduction (p<0.032) was observed by the second method analysis of the VLA-4+/CD19+ B cell number data.

In other analysis, reductions in VLA-4 MFI were only observed in B cells at week 16 (<10% reduction).

T Cell Surface VLA-4 Effects

ATL1102 treatment resulted in a reduction in the percentages of CD3+ and CD4+ cells expressing detectable levels of VLA-4. When analysing data at week 12 compared to baseline, the second method of analysis showed a reduction in the percentage of CD3+ T lymphocytes that were also VLA-4+ (8.2% reduction p<0.037) and a reduction in the percentage of CD4+ T lymphocytes that were also VLA-4+ (12% reduction p<0.047).

Conclusion

ATL1102 reduces VLA-4 on a select number of blood B cells and T cells.

Example 5: Human Blood Cell Pharmacodynamic Studies

Blood samples were obtained on visits 2, 6, 7, and 8 from the RRMS patients in example study 2 for evaluating blood cell changes. Cell changes were assessed using multi-channel flow cytometry as per example 4 and by hematology.

CD8+/CD4+ Measurements:

For evaluation of CD8+/CD4+ cell count, blood samples were assayed by flow cytometry at visits 2, 6, 7, and 8 using the 36 ml blood samples obtained for VLA-4 assay. The ratio of CD4:8 did not change in these studies.

Cell Counts: Leukocytes

Blood samples were assayed at visits 2, 6, 7, and 8 by hematology and Multi-channel flow cytometry. The following reductions versus placebo were observed at week 8 of treatment with ATL1102 (using the first method of analysis)

Total leucocytes: 37% (p<0.0005)
Granulocytes: 43% (p<0.0005)
Lymphocytes: 25% (p<0.05)
B cells: 53% (p<0.0005)
HLA-DR+ B cells: 41% (p<0.05)
CD4+ T cells: 26% (p<0.05)
CD8+ T cells: 23% (p<0.05)

There was also a possible increase in the proportion of CD8+CD25+ T cells (p<0.05) and CD8+HLA-DR+ T cells (p<0.005) although there were small numbers of these cells.

Conclusion

ATL1102 reduces the number of B cells, T cells and granulocytes (including neutrophils, basophils, and eosinophils (data not shown). ATL1102 does not reduce the number of monocytes, or NK lymphocytes. This data is surprising given that antibodies to VLA-4 would usually increase the number of these cells in the blood (see Example 8).

VLA-4 is known to have a role in the maturation, apoptosis, activation, adhesion and migration of B and T cells (Arroyo et al., 1996; Carrasco and Batista, 2006; Lo et al., 2003; Alter et al., 2003 Tchilian et al., 1997; Nino et al., 2006), one or more of which could contribute to the cellular pharmacodynamic observations in the ATL1102 phase II study. VLA-4 also has a role on neutrophil precursors, eosinophils and basophils.

ATL1102 derived CD34+ stem and progenitor cells may have few contaminating blood cells that cause autoimmune disease allowing the patients own CD34+ cell to be used in autologous treatment of autoimmune diseases post irradiation. Additionally ATL1102 stem and progenitor cells harvested according to methods of the disclosure may have fewer contaminating cells with a role in graft versus host disease, allowing better allogenic treatments of leukamias. Unaffected natural killer and dendritic (monocyte) cells in the graft improves disease free survival. ATL1102 reduces VLA-4 on a select number of blood B cells and T cells which reduces the potential to release tumor cells in patients.

Example 6: Human ATL1102 Pharmacokinetics Studies

Blood samples (7 ml) were obtained on visits 2, 5, 6, and 8 for evaluating oligonucleotide 1 plasma levels. On visits 2, 5, and 6 this was performed prior to and 1, 2, 3, 4, and 6 hours after injection of oligonucelotoide 1/placebo. On visit 8, a single sample was obtained. The blood samples after drawing were centrifuged for 10 minutes at 1,600 g and at a temperature of 4° C. 10 minutes. The supernatant was transferred to labeled polypropylene tubes (2 tubes per sample) by pipetting and further transferred to a deep-freezer for storing at a temperature of −20° C. (tolerance +5° C.) or lower.

Pharmacokinetic Data

Median profiles of ATL1102 show no indication of accumulating peak or total plasma exposure levels from day 1 to week 8 (FIG. 1 and Table 5).

The increase in $C_{min}$ concentrations during the treatment phase suggests that oligonucleotide 1 accumulates in tissue with multiple dose administrations. The decrease in $C_{min}$ concentrations during the follow-up phase suggests that the $t_{1/2}$ elimination is approximately 3 weeks.

TABLE 5

Table III.
PK Parameters of OLIGONUCLEOTIDE 1

| | |
|---|---|
| $C_{max}$ | 10157-10895 ng/mL (mean) |
| $T_{max}$ | 3 hrs (median) |
| $AUC_{last}$ | 46587-48521 h · ng/mL (mean) |

Median plasma concentrations of ATL1102 were determined at serial measurements on day 1 and in week 4 and week 8. After subcutaneous administration, ATL1102 appeared to be rapidly absorbed with measurable concentrations seen at the first post-dose timepoint (1 hour post-dose). Subsequently, all median profiles showed a clear increase from 1 to 2 hours. The day 1 median profile further increased noticeably from 2 to 3 hours post-dose. This was not the case for the week 4 and week 8 median profiles. ATL1102 peak plasma concentrations of the median profiles were attained 2 to 4 hours after injection and declined thereafter with the 6 hour values being clearly below the 4 hour values for all median profiles. Median predose ATL1102 concentrations in week 4 and week 8 were about 100-fold lower than the median concentrations 6 hour after dosing on day 1 and in week 4, respectively.

In general, with subcutaneous administration of ATL1102 three times in week 1 and twice weekly in weeks 2 to 8, there was no indication of accumulating peak ($C_{max}$) or total (AUC) plasma exposure levels from day 1 to week 8. However, trough (pre-dose) concentrations clearly increased from week 4 to week 8. Median trough values were 38 ng/mL and 88 ng/mL at week 4 and week 8, respectively. At week 8 all 32 patients had trough levels above their trough levels at week 4. Following planned treatment discontinuation at week 8, ATL1102 median plasma concentrations were 32 ng/mL at week 12 (4 weeks post-dose), and 11 ng/mL at week 16 (8 weeks post-dose).

The pharmacokinetic parameters were calculated from the individual plasma concentration profiles. A total of 100 profiles were evaluated, 34 profiles each at day 1 and week 4 and 32 profiles at week 8.

$C_{max}$ (peak exposure) values ranged from 2889 ng/mL to 24118 ng/mL. The median values were 9773 ng/mL at day 1, 10505 ng/mL at week 4, 9462 ng/mL at week 8, and 9848 ng/mL overall.

The maximum concentration of ATL1102 was observed at an average of 3.3 hours post-dose (day 1), 2.7 hours post-dose (week 4), and 3.2 hours post-dose (week 8). Considering all 100 plasma concentration profiles, the maximum concentration was observed at 2 hours in 28 profiles, at 3 hours in 41 profiles, and at 4 hours in 27 profiles. The median $t_{max}$ was approximately 3 hours after administration of ATL1102.

The individual values of $AUC_{last}$ (total exposure) ranged from 13374 hxng/mL to 110909 hxng/mL. The $AUC_{last}$ values did not indicate an accumulating effect from day 1 to week 8. The median values were 45847 hxng/mL at day 1, 46074 hxng/mL at week 4, 45344 hxng/mL at week 8, and 45976 hxng/mL overall.

A total of 18 patients had both a week 12 and week 16 measurement of ATL1102 plasma concentrations, which allowed a rough estimate of the terminal elimination half-life $t_{1/2}$. The calculated elimination half-lives ranged from 1.8 to 20 weeks with a median of 3.0 weeks, a geometric mean of 3.2 weeks, and a coefficient of variation of 106%. The log-transformed half-lives had a SD of 0.564.

The ATL1102 plasma concentrations appear to be higher in female patients than in male patients by a factor of approximately 1.6. The geometric means of the $AUC_{last}$ and $C_{max}$ values were 1.5 to 1.8-fold higher in female patients than in male patients. Future studies with larger number of patients are needed to confirm this apparent gender difference in exposure.

Conclusion

Maximum plasma ATL1102 concentrations were reached about 3 hours after administration and ranged from 2889 ng/mL to 24118 ng/mL. (median 9848 ng/mL). The area under the plasma concentration time curve until 6 hours post administration ranged from 13374 hxng/mL to 110909 hxng/mL (median 45976 hxng/mL). There was no indication of accumulating peak ($C_{max}$) or total (AUC) plasma exposure levels from day 1 to week 8. Median pre-dose concentrations in week 4 and week 8 were about 100 fold lower than the median concentrations 6 hours after the dosing on day 1 and in week 4, respectively. There was an increase in pre-dose concentrations from week 4 (median 38 ng/mL) to week 8 (median 88 ng/mL), suggesting ATL1102 accumulation in tissue upon multiple dose administration. The median terminal elimination half-life estimated from only 2 points (4 and 8 weeks after the last administration) was 3 weeks.

Example 7: ATL1102 Pharmacokinetics Studies in Rats

Sprague-Dawley rats were injected with single intravenous bolus injections of $^3$H-ATL1102 (ISIS107248). The mean concentration of radioactivity in plasma, blood and tissues determined at a mean dose of 5 mg/Kg in male rats using liquid scintillation counting. Table 6 below presents summary information of the ATL1102 blood/plasma and tissue concentration measurements by the minute (min) and hour (hr) or days (d). Blood and plasma are microgram equivalents/ml and tissue concentrations are microgram equivalents per gram of tissue.

ATL1102 is removed quickly within 4 hours from the blood and plasma to the organs such as the kidney, liver, and primary and secondary immune organs including bone marrow (BM) and Lymph nodes (LN). In the BM excluding femur (BM exf), it had a half life of about 14 days. In the BM femur the half life was longer.

TABLE 6

| Sample | 2 min | 10 min | 30 min | 45 min | 1 hr | 3 hr | 4 hr | 6 hr | 8 hr | 12 hr | 48 hr 2 d | 72 hr 3 d | 168 hr 7 d | 336 hr 14 d |
|---|---|---|---|---|---|---|---|---|---|---|---|---|---|---|
| Blood | 87.3 | 60.4 | 32.9 | 23.1 | 16.9 | 2.3 | 1.1 | 0.7 | 0.5 | 0.5 | 0.6 | 0.6 | 0.5 | 0.3 |
| Plasma | 50.2 | 36.7 | 19.6 | 13.8 | 10.2 | 1.4 | 0.7 | 0.5 | 0.4 | 0.4 | 0.5 | 0.5 | 0.4 | 0.3 |
| BM exf | | | | | | 7.0 | | | | | 6.1 | 5.3 | 4.0 | 2.9 |
| BMfemur | | | | | | 6.2 | | | | | 7.9 | 8.2 | 7.1 | 6.0 |
| Kidney | | | | | | 85.4 | | | | | 83.7 | 78.9 | 72.3 | 55.3 |
| Liver | | | | | | 12.0 | | | | | 10.2 | 8.5 | 6.5 | 4.0 |
| LN mand | | | | | | 6.4 | | | | | 7.2 | 7.4 | 7.7 | 3.9 |
| Spleen | | | | | | 4.7 | | | | | 5.5 | 5.5 | 4.7 | 4.3 |
| Prostate | | | | | | 4.3 | | | | | 3.7 | 3.0 | 2.3 | 1.5 |
| Stomach | | | | | | 3.1 | | | | | 2.5 | 2.2 | 1.6 | 1.2 |
| Thymus | | | | | | 0.7 | | | | | 1.2 | 1.2 | 1.1 | 0.9 |

No sample was collected where there are blank spaces;
LN mand, is the mandibular lymph node.

Male Sprague-Dawley rats were injected with single 19.3 mg/Kg intravenous bolus injections of $^3$H-ATL1102 (ISIS107248) and female rats were injected with single 19.7 mg/Kg doses. The mean concentration of radioactivity in plasma, blood and bone marrow, kidney and liver is shown below at 4 and 24 hour in Table 7. ATL1102 is lower in plasma than the organs at 4 hours and by 24 hours appears mostly in the kidney liver and bone marrow. In the various bone marrow samples analyzed from different sites, the levels of drug are about the same as liver on a microgram equivalent/gram of tissue in both males and females.

TABLE 7

| | Male | | Female | |
|---|---|---|---|---|
| Sample | 4 hr | 24 hr | 4 hr | 24 hr |
| Plasma | 8.3 | 1.9 | 18.4 | 1.5 |
| BM vertebra | 20.4 | 18.1 | 18.8 | 24.9 |
| BM femoral head | 61.9 | 24.3 | 28.2 | 14.2 |
| BM humerous head | 28.1 | 20.2 | 16.9 | 21.5 |
| Kidney | 71.2 | 98.1 | 71.2 | 145.8 |
| Liver | 30.0 | 33 | 30.1 | 49.5 |

Example 8: Comparative Human Mature Blood Cell Pharmacodynamic and Pharmacokinetics of an Antisense to VLA-4 Compared to an Antagonist to VLA-4

The novel mechanisms of action of VLA-4 antisense drugs including differentiated pharmacodynamics and pharmacokinetics provide benefits in stem cell/progenitor cell mobilizations used alone and in combination with mobilizing agents G-CSF and/or Mozobil™, particularly when compared to the potential use of VLA-4 antagonist small molecules and antibodies.

Tysabri™, is a monoclonal antibody to the VLA-4 target on the market for the treatment of relapse remitting multiple sclerosis (RRMS) when other treatments like interferon beta or copaxone fail. Tysabri™ treatment in volunteers and in RRMS affects all VLA-4$^+$ leukocytes in the blood and leads to peripheral sequestration of immune cells. It increases circulating lymphocytes (1.5 fold), including CD4$^+$, CD8$^+$ and natural killer cells, and B cells more than other lymphocytes (2.8 fold). Tysabri™ increases monocytes, and of the granulocytes increases the eosinophils and basophils, without elevating neutrophils which in humans are virtually all VLA-4 negative (Krumholz et al., 2008; Polman et al., 2006; Putzki et al., 2010; Kivisaak et al., 2009). Tysabri™ has a long half life in blood and prolonged effect of more than a month. It is a potent immunosuppressive drug with the ability to cause JC virus activation and progressive multifocal leukoencephalitis (PML).

In contrast, ATL1102, an antisense drug to VLA-4, reduces circulating B cells, CD4$^+$ T cells, CD8+ T cells and granulocytes, including neutrophils, eosinophils and basophils, and has no effect on monocytes and natural killer cells cell numbers in the blood. ATL1102 has a very short half-life in plasma and is rapidly cleared to organs within hours limiting exposure of circulating leukocytes to the drug. These pharmacokinetics, select effect on certain mature blood cells and more select VLA-4 pharmacodynamic effects of treatment outlined in the Example 4 preserves in most blood cells the VLA-4 mediated capacity of adhesion and immunosurveillance.

Example 9: ATL1102 Phase I Study

The primary objective of this study was to assess the safety and tolerability of single doses and multiple doses of ATL 1102 given on an escalation dose regimen and injected subcutaneously (SC) to healthy volunteers. Both males and females were entered into the study.

Dosing Regimens

The single subcutaneous injection doses in males in the dose escalation study were 0.1 mg/Kg, 0.5 mg/Kg, 1.0 mg/Kg, 2.0 mg/Kg, 4.0 mg/Kg and 6.0 mg/Kg. A single intravenous infusion dose in males of 2.0 mg/Kg was also administered over 60 minutes. The multiple subcutaneous injection doses in females were 4.0 mg/Kg administered on days 1, 3, and 5 and 6.0 mg/Kg administered on days 1, 3, and 5.

Subjects were randomised to receive active drug or placebo in a blinded study. Subjects attended the Unit for a single study period. For the escalation single dose schedule, subjects were admitted on the afternoon prior to dosing (day 1) and were discharged, at the discretion of the investigator, approximately 24 hours after dosing was completed. The multiple dose schedule subjects were discharged 24 hours after the third dose. The subjects then returned for a number of outpatient visits (includes up to week 59 for collection of blood samples for pharmacokinetics).

The ATL1102 dose was administered by a doctor or nurse as a subcutaneous injection or as an intravenous infusion made up to 100 mL with 0.9% NaCi (saline) over 60 minutes (group 7). The subjects were recumbent or semi-recumbent throughout the infusion.

Subjects were requested to remain recumbent/semi-recumbent for at least 4 hours from the time of dosing. The actual time of the start (and end for group 7 only) of each dose were recorded in the CRF.

Subsequent Study Days

All subjects returned for blood samples for ATL1102 on days 4, 8, 15, 22 and 29 and subjects dosed from 2 mg/Kg upwards also returned on days up to day 59 for ATL1102 pharmokinetics samples. Vital signs (blood pressure and pulse) were obtained from all groups on days 4, 8 and 15. Blood samples for safety laboratory tests were performed 24 hours post dose (days 4, 8, 15 and follow up).

Follow Up

A physical examination including blood pressure, temperature and pulse rate, a 12-lead ECG and laboratory safety tests (haematology, clinical chemistry and urinalysis).

Blood sample for ATL1102 was performed at the subject visit on day 29 for subjects receiving up to 1 mg/Kg and then on day 59 for subjects receiving 2 mg/Kg upwards. Similar assessments were done for multidose studies subjects. Adverse events were assessed at this visit.

Pharmacokinetic/Pharmacodynamic Sampling

Blood samples for ATL1102 assay required (3 ml) to be taken to provide approximately 1.6 ml of plasma. Samples were collected in lavender top 4.5 ml EDTA tubes at pre-dose (baseline) and at 30, 60 and 90 minutes and 2, 2.5, 3, 4, 6, 12, 24 hours and 4, 8, 15, 22, and 29 days post dose for groups 1-3.

For subjects receiving 2 mg/Kg to 6 mg/Kg single sc doses the samples were also taken on days 43, and 59.

For subjects receiving the 2 mg/Kg iv dose samples were taken at pre dose, 30, 60, 70 and 90 minutes post start of infusion and at 2, 3, 4, 6, 8 and 24 hours, and also on days 2, 4, 8, 15, 22, 29, 43, and 59 post dose.

For subjects receiving the multiple sc doses the blood samples were taken on day 1 (after the first dose) and day 5 (after the third dose) for 24 hour drug level profiling on each occasion, and then at different time points, at least up to day 59 post dose.

Laboratory Tests

Haematology: Hb, Hct, MCV, MCH, MCHC, RBC, WBC and differential, Platelets, PT, APTT, TT.

Biochemistry: Na, K, Creatinine, Fasting Glucose, AP, AST, ALT, GGT total protein, albumin, bilirubin, urea, complement.

Urine: spec. gravity, pH, protein, glucose, blood, ketones. (using 10 sg multisticks). If abnormal dipstick result occurs, urine was sent for microscopy and culture.

Results

There was no increase in the level of white blood cells and no effect on red blood cells or platelets in the short ATL1102 phase I study, even with multiple doses at 4 and 6 mg/Kg.

Example 10: Stem/Progenitor Cell Mobilization in Healthy Volunteers, Non Hodgkin's Lymphoma (NHL) Patients and Multiple Myeloma (MM) Patients ATL1102 will be administered to healthy volunteers, non-Hodgkin's lymphoma (NHL) patients, Multiple Myeloma (MM) patients, to release stem/progenitor cells. It may be administered alone, together with G-CSF agonists, together with Mozobil™, or together with G-CSF plus Mozobil™ or other mobilizing treatments to provide superior mobilization.

Described below is a method for the release of stem and/or progenitor cells using ATL1102 and the G-CSF analogue Neupogen™. The study is designed with a control to show ATL1102+G-CSF is superior to mobilization with G-CSF alone in the release of CD34$^+$ hematopoietic stem and/or progenitor cells. An alternative to daily Neupogen™ (filgastrim) is a single dose of pegfilgrastim (pegylated G-CSF analogue, Neulasta™) long acting G-CSF-Peg dosed once.

Primary Objective;

To show ATL1102+Neupogen™ hematopoietic progenitor cell mobilization is safe, effective, and superior to mobilization with Neupogen™ alone.

Dosing Regimen 1; ATL1102 and G-CSF Treatment Schedule

Two groups of subjects (10 per group) are treated with daily injections of filgrastrim (G-CSF analogue, agonist Neupogen™) for a period of 4, 5, 6, or 7 days, or as recommended by the manufacturer. Neupogen™ is typically injected sc 10 μg/kg/day daily over 4 days before the first apheresis procedure on day 5, and optionally, on day 5, 6 and 7 if not enough stem/progenitor cells are released.

One group is additionally treated with ATL1102, the hVLA-4 antisense compound, whilst the other group is injected with saline. The hVLA-4 antisense compound is injected to obtain a final antisense dose of 4 mg/kKg per day. The hVLA-4 antisense compound will be injected daily over 4, 5, 6 or 7 days for a total of 4, 5, 6 or 7 doses or the maximum tolerated dose. The first apheresis procedure is on day 5, and follow up apheresis on days 6 and 7, and if not enough stem cell/progenitor cells are released, apheresis may conducted daily to day 14.

The study is designed to measure the number of CD34$^+$ stem/progenitor cells mobilized/kg in a Neupogen™ regimen including ATL1102, the number of aphereses required to collect a target number of stem/progenitor cells, time to engraftment and safety.

Dosing Regimen 2; ATL1102 and G-CSF Treatment Schedule

Two groups of subjects (10 per group) are treated with daily injections of filgrastrim (G-CSF analogue, agonist Neupogen™) for a period of 4, 5, 6, or 7 days, or as recommended by the manufacturer. Neupogen™ is typically injected sc 10 μg/kg/day daily over 4 days before the first apheresis procedure on day 5, and optionally, on day 5, 6 and 7 if not enough stem/progenitor cells are released.

One group is additionally treated with ATL1102, the hVLA-4 antisense compound, whilst the other group is injected with saline. The hVLA-4 antisense compound is injected to obtain a final antisense dose of 4 or 6 mg/Kg per day. The hVLA-4 antisense compound will be injected every other day on day 1, 3, 5, for a total of 3 doses or the maximum tolerated dose. The first apheresis procedure is on day 5, and follow up apheresis on days 6 and 7, and if not enough stem cell/progenitor cells are released, apheresis may conducted daily to day 14.

The study is designed to measure the number of CD34$^+$ stem/progenitor cells mobilized/kg in a Neupogen™ regimen including ATL1102, the number of aphereses required to collect a target number of stem/progenitor cells, time to engraftment and safety.

Laboratory Tests

The following tests may be performed.

Flow cytometric analysis of living cells may be performed with various stem cell/progenitor surface markers to obtain information on the number and type of CD34$^+$ stem cell/progenitor released and other surface markers may be used to assess the leukocyte populations in the blood;

Clonogenic assays will be performed to determine the clonogenic progenitors including multipotential/oligopotential CFU-GEMM, erythroid (BFU-E), granulocyte-monocyte (CFU-GM), and megakaryocyte (CFU-Mk). Peripheral blood cells will be plated with various factors and the Colony Forming Units determined on the cultures;

Stem cell engraftment into mice; the engraftment potential of human peripheral blood stem cell/progenitor cells mobilized and collected may be determined in a NOD-SCID/2m$^{-/-}$ mouse model;

Stem cell engraftment into humans; the engraftment potential of human peripheral blood stem cell/progenitor cells mobilized and collected will be determined in patients after high dose chemotherapy; The speed of platelet recovery and neutrophil recovery will be explored as well as the long term graft potential;

Hematology may be performed to assess the leukocyte, platelet, and red blood cell populations in the blood;

The safety of ATL1102 treatment used with Neupogen™ will be assessed to determined whether there are any drug related serious adverse events.

Outcomes

Efficacy variables: The percentage of volunteers or patients that have achieved 2×10$^6$ CD34$^+$ cells per Kg. The percentage who have achieved >5×10$^6$ CD34$^+$ cells per Kg of body weight in, for example, 4 or fewer aphereses in NHL, and percentage of patients with >6×10$^6$ CD34$^+$ cells per Kg of body weight in, for example, 2 or fewer aphereses in MM. Assess if engraftment is prompt and durable;

Safety variables; Lymphoma mobilization will be assessed and major toxicities observed.

The above study is expected to show volunteer and patients who are given ATL1102+Neupogen™, compared to Neupogen™ alone, have more stem and/or progenitor cells available for transplantation.

The above study is expected to determine the number of apheresis collections needed to obtain the target number of stem and/or progenitor cells required for transplantation.

Studies will also assess the number of days it takes for stem and/or progenitor cells to re-engraft in patients who are mobilized with ATL1102+Neupogen™ compared to Neupogen™ alone.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

All publications discussed and/or referenced herein are incorporated herein in their entirety.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

REFERENCES

Alter et al., J. Immunol. (2003) 170:4497-4505
Altschul et al., J. Mol. Biol. (1990) 215:403-410
Arroyo et al., Cell (1996) 85:997-1008
Carrasco and Batista, EMBO (2006) 25:889-899
Colquehoun et al., Transplantation (1993) 56:755-758
Diflo et al., Hepatology (1992) 16:PA278
Elbashir et al., Nature (2001a) 411:494-498
Elbashir et al., Genes Dev. (2001b) 15:188-200
Englisch et al., Angewandte Chemie, International Edition (1991) 30:613
Fire et al., Nature (1998) 391:806-811
Fukunaga et al., Cell (1993) 74:1079-1087
Gabrilove, Sem. Hematol. (1989) 26:1-14
Guo and Kempheus, Cell (1995) 81:611-620
Jones et al., Bailliere's Clin. Hematol. (1989) 2:83-111
Kivisaak et al., Neurol. (2009) 72(22):1922-30
Kocher et al., Nature Med. (2001) 7:430-436
Krumbholz et al., Neurology (2008) 71:1350-1354
Kuga et al., Biochem. Biophys. Res. Comm. (1989) 159: 103-111
Lachaux et al., J. Ped. (1993) 123:1005-1008
Livak and Schmittgen, Methods (2001) 25:402-408
Lo et al., J. Exp. Med. (2003) 197(3):353-361
Lu et al., Arch. Biochem. Biophys. (1989) 268: 81-92
Martin et al., Helv. Chim. Acta (1995) 78:486-504
Montgomery et al., Proc. Natl. Acad. Sci. USA. (1998) 95:15502-15507
Moore et al., Proc. Natl. Acad. Sci. USA (1987) 84:7134-7138
Nielsen et al., Science (1991) 254, 1497-1500
Nino et al., Ann. Neurol. (2006) 59:748-754
Oppliger et al., Hematologica (2005) 90(7):875-880
Polman et al., N. Eng. J. Med. (2006) 354:899-910
Putski et al., Eur. Neurol. (2010) 63:311-317
Simmons et al., Blood (1992) 80:388-395
Souza et al., Science (1986) 232:61-65
Tabara et al., Science (1998) 282:430-431
Takano et al., Curr. Pharm. Des. (2003) 9:1121-1127
Tchilian et al., Immunology (1997) 92:321-327
Teixido et al., J. Clin. Invest. (1992) 90:358-367
Tijsterman et al., Science (2002) 295:694-697
Timmons and Fire, Nature (1998) 395:854
Tuschl et al., Genes Dev. (1999) 13:3191-3197
Welte et al., Proc. Natl. Acad. Sci. USA (1985) 82:1526-1530
Wendel et al., J. Immunol. (1992) 149:918-924
Williams et al., Nature (1991) 352:438-441
Wright et al., Hepatology (1991) 14:PA48
Zhang and Madden, Genome Res. (1997) 7:649-656

The invention claimed is:

1. A method for reducing the number of circulating leukocytes in a human subject in need thereof, the method comprising:
   identifying a human subject in need of a reduction in the number of circulating leukocytes, and
   administering to said identified subject an effective amount of a composition comprising an antisense oligonucleotide to human CD49d.

2. The method of claim 1, wherein the circulating leukocytes are selected from the group consisting of B-cells, T-cells, and granulocytes.

3. The method of claim 1, further comprising monitoring the number of CD49d positive and CD49d negative B-cells, T-cells and/or granulocytes in the peripheral blood.

4. The method of claim 3, wherein the subject has elevated circulating leukocytes due to an autoimmune and/or inflammatory condition.

5. The method of claim 1, wherein the circulating leukocytes are CD49d positive.

6. The method of claim 2, wherein the granulocytes are eosinophils, basophils or neutrophils.

7. The method of claim 3, wherein the granulocytes are eosinophils, basophils or neutrophils.

8. The method of claim 1, wherein said an antisense oligonucleotide comprises:

(SEQ ID NO: 1)
5'-$^{Me}C^{Me}U$G AGT $^{Me}$CTG TTT $^{Me}U^{Me}C^{Me}C$ A$^{Me}U^{Me}U$ $^{Me}C^{Me}U$-3' wherein,
   a) each of the 19 internucleotide linkages of the oligonucleotide is an O,O-linked phosphorothioate diester;
   b) the nucleotides at the positions 1 to 3 from the 5' end are 2'-O-(2-methoxyethyl) modified ribonucleosides;
   c) the nucleotides at the positions 4 to 12 from the 5' end are 2'-deoxyribonucleosides;
   d) the nucleotides at the positions 13 to 20 from the 5' end are 2'-O-(2-methoxyethyl) modified ribonucleosides; and
   e) all cytosines are 5-methylcytosines ($^{Me}C$),
or a pharmaceutically acceptable salt thereof.

* * * * *

SEQUENCE LISTING

```
<160> NUMBER OF SEQ ID NOS: 2

<210> SEQ ID NO 1
<211> LENGTH: 20
<212> TYPE: DNA
<213> ORGANISM: Artificial Sequence
<220> FEATURE:
<223> OTHER INFORMATION: antisense oligonucleotide
<220> FEATURE:
<221> NAME/KEY: modified_base
<222> LOCATION: (1)..(1)
<223> OTHER INFORMATION: methylcytosine
<220> FEATURE:
<221> NAME/KEY: modified_base
<222> LOCATION: (1)..(3)
<223> OTHER INFORMATION: 2'-O-(2-methoxyethyl) modified ribonucleosides
<220> FEATURE:
<221> NAME/KEY: modified_base
<222> LOCATION: (2)..(2)
<223> OTHER INFORMATION: methyluracil
<220> FEATURE:
<221> NAME/KEY: modified_base
<222> LOCATION: (4)..(13)
<223> OTHER INFORMATION: 2'deoxyribonucleosides
<220> FEATURE:
<221> NAME/KEY: modified_base
<222> LOCATION: (7)..(7)
<223> OTHER INFORMATION: methylcytosine
<220> FEATURE:
<221> NAME/KEY: modified_base
<222> LOCATION: (13)..(13)
<223> OTHER INFORMATION: methyluracil
<220> FEATURE:
<221> NAME/KEY: modified_base
<222> LOCATION: (14)..(14)
<223> OTHER INFORMATION: methylcytosine
<220> FEATURE:
<221> NAME/KEY: modified_base
<222> LOCATION: (14)..(20)
<223> OTHER INFORMATION: 2'-O-(2-methoxyethyl) modified ribonucleosides
<220> FEATURE:
<221> NAME/KEY: modified_base
<222> LOCATION: (15)..(15)
```

```
<223> OTHER INFORMATION: methylcytosine
<220> FEATURE:
<221> NAME/KEY: modified_base
<222> LOCATION: (17)..(17)
<223> OTHER INFORMATION: methyluracil
<220> FEATURE:
<221> NAME/KEY: modified_base
<222> LOCATION: (18)..(18)
<223> OTHER INFORMATION: methyluracil
<220> FEATURE:
<221> NAME/KEY: modified_base
<222> LOCATION: (19)..(19)
<223> OTHER INFORMATION: methylcytosine
<220> FEATURE:
<221> NAME/KEY: modified_base
<222> LOCATION: (20)..(20)
<223> OTHER INFORMATION: methyluracil

<400> SEQUENCE: 1
cugagtctgt ttccauucu                                                    20

<210> SEQ ID NO 2
<211> LENGTH: 20
<212> TYPE: DNA
<213> ORGANISM: Artificial Sequence
<220> FEATURE:
<223> OTHER INFORMATION: antisense oligonucleotide
<220> FEATURE:
<221> NAME/KEY: modified_base
<222> LOCATION: (1)..(5)
<223> OTHER INFORMATION: 2'-O-(2-methoxyethyl) modified ribonucleosides
<220> FEATURE:
<221> NAME/KEY: modified_base
<222> LOCATION: (6)..(15)
<223> OTHER INFORMATION: 2'deoxyribonucleosides
<220> FEATURE:
<221> NAME/KEY: modified_base
<222> LOCATION: (9)..(9)
<223> OTHER INFORMATION: methylcytosine
<220> FEATURE:
<221> NAME/KEY: modified_base
<222> LOCATION: (10)..(10)
<223> OTHER INFORMATION: methylcytosine
<220> FEATURE:
<221> NAME/KEY: modified_base
<222> LOCATION: (12)..(12)
<223> OTHER INFORMATION: methylcytosine
<220> FEATURE:
<221> NAME/KEY: modified_base
<222> LOCATION: (13)..(13)
<223> OTHER INFORMATION: methylcytosine
<220> FEATURE:
<221> NAME/KEY: modified_base
<222> LOCATION: (16)..(20)
<223> OTHER INFORMATION: 2'-O-(2-methoxyethyl) modified ribonucleosides
<220> FEATURE:
<221> NAME/KEY: modified_base
<222> LOCATION: (18)..(18)
<223> OTHER INFORMATION: methylcytosine
<220> FEATURE:
<221> NAME/KEY: modified_base
<222> LOCATION: (19)..(19)
<223> OTHER INFORMATION: methylcytosine
<220> FEATURE:
<221> NAME/KEY: modified_base
<222> LOCATION: (20)..(20)
<223> OTHER INFORMATION: methylcytosine

<400> SEQUENCE: 2
atatttttcc acctgtgccc                                                   20
```